United States Patent
Nguyen

(10) Patent No.: US 10,398,709 B2
(45) Date of Patent: Sep. 3, 2019

(54) COMPOSITIONS FOR THE TREATMENT OF CATARACTS

(71) Applicant: Catacore, Inc., West Richland, WA (US)

(72) Inventor: Sam L. Nguyen, Saratoga, CA (US)

(73) Assignee: Catacore, Inc., West Richland, WA (US)

( * ) Notice: Subject to any disclaimer, the term of this patent is extended or adjusted under 35 U.S.C. 154(b) by 0 days.

(21) Appl. No.: 15/221,550

(22) Filed: Jul. 27, 2016

(65) Prior Publication Data

US 2017/0027961 A1   Feb. 2, 2017

Related U.S. Application Data

(60) Provisional application No. 62/295,267, filed on Feb. 15, 2016, provisional application No. 62/252,120, filed on Nov. 6, 2015, provisional application No. 62/202,518, filed on Aug. 7, 2015, provisional application No. 62/197,477, filed on Jul. 27, 2015.

(51) Int. Cl.
| | |
|---|---|
| A61K 31/575 | (2006.01) |
| A61K 9/00 | (2006.01) |
| A61K 47/10 | (2017.01) |
| A61K 47/38 | (2006.01) |
| A61K 9/08 | (2006.01) |
| A61K 9/51 | (2006.01) |

(52) U.S. Cl.
CPC ......... *A61K 31/575* (2013.01); *A61K 9/0048* (2013.01); *A61K 9/0051* (2013.01); *A61K 9/08* (2013.01); *A61K 9/5153* (2013.01); *A61K 47/10* (2013.01); *A61K 47/38* (2013.01)

(58) Field of Classification Search
None
See application file for complete search history.

(56) References Cited

U.S. PATENT DOCUMENTS

| 2002/0132758 A1 | 9/2002 | Shell |
| 2014/0031327 A1 | 1/2014 | Gestwicki |

FOREIGN PATENT DOCUMENTS

| WO | WO-2014015024 A2 * | 1/2014 | ........... A61K 31/045 |
| WO | WO2014/035451 A1 | 3/2014 | |
| WO | WO2016029197 A1 | 2/2016 | |
| WO | WO2016029199 A1 | 2/2016 | |

OTHER PUBLICATIONS

Jung et al. ("Prednisolone 21-sulfate sodium: a colon-specific pro-drug of prednisolone"; 2003; Journal of Pharmacy and Pharmacology; 55:1075-1082) (Year: 2003).*
Ren et al. ("Sulfated oxysterol, 25HC3S, is a potent regulator of lipid metabolism in human hepatocytes" 2007; Biochemical and Biophysical Research Communications; 360: 802-808 (Year: 2007).*
Badaro et al. ("Retinal Biocompatibility of Brilliant Blue G with Deuterated Water for Chromovitrectomy"; 2014; J. Opthalmic Vis. Res.; 9(2): 204-209 (Year: 2014).*
Colitz, et al. (Estradiol Biosynthesis in Canine Lens Epithelial Cells; 2015; Current Eye Research; 40(5): 541-548 (Year: 2014).*
L. N. Makley et al., Pharmacological chaperone for alpha-crystallin partially restores transparency in cataract models, Science, Nov. 6, 2015, vol. 350, Issue 6261, 674-677.
X. Li et al., Biosynthesis of the regulatory oxysterol, 5-cholesten3b,25-diol-3-sulfate, in hhepatocytes, Journal of Lipid Research, vol. 48, 2007, 2587-2596.
H. Girao et al., Cholesterol Oxides Accumulate in Human Cataracts, Exp. Eye Res., 1998, 66, 645-652.
S. Ren et al., Identification of Novel Regulatory Cholesterol Metabolite, 5-Cholesten, 3b,25-Diol, Disulfate, PLOS, Jul. 2014, vol. 9, Issue 7, e103621.
Shanmugam et al, Effect of lanosterol on human cataract nucleus, Indian J. Ophthalmol., Dec. 2015; 63(12): 888-890.
Zhang et al, Lanosterol reverses protein aggregation in cataracts, Nature, Jul. 30, 2015; 523(7562):607-11.
Abelson, M.B., Normal human tear pH by direct measurement, Arch Ophthalmol, Feb. 1981; 99(2); 301.

* cited by examiner

*Primary Examiner* — Timothy P Thomas
(74) *Attorney, Agent, or Firm* — Sam L. Nguyen

(57) ABSTRACT

In one embodiment, the present application discloses an aqueous ophthalmic composition for the treatment of eye diseases, lesions and injuries, comprising: a) one steroid, or a combination of at least two steroids selected from the group consisting of lanosterol, dihydrolanosterol, 4,4-dimethylcholesta-8(9),14,24-trien-3β-ol, 4,4-dimethylcholesta-8,24-dien-3β-ol, 4,4-dimethylcholesta-8-en-3β-ol, 4,4-dimethylcholesta-8(9),14-dien-3β-ol, 14-desmethyl lanosterol, lathosterol, $\Delta^{7,24}$-cholestadienol, cholesterol, cholesta-7-enol, cholesteryl ester, 7-dehydrocholesterol, desmosterol, 7-dehydrodesmosterol, zymosterol, 27-hydroxycholesterol, cholesta-7,24-dien-3-β-ol, cholesta-8(9)-en-3-β-ol, 5α-cholestan-3β-ol-6-one, 5-cholesten-3β,25-diol, 5-cholesten-3β,25-OSO₃H (5-cholesten-3β,25-sulfate), 5-cholesten-3β-OSO₃H,25-ol (5-cholesten-3β-sulfate,25-ol), 5-cholesten-3β,25-diol, disulfate, and their esters thereof, or a pharmaceutically acceptable salt thereof, in a concentration effective for the treatment and/or prophylaxis of the eye diseases, lesions and injuries; and b) a pharmaceutical excipient; and methods of treatment using such compositions.

8 Claims, 1 Drawing Sheet

RESULTS:
| Days | Dog 1 | | Dog 2 | | Dog 3 | |
|---|---|---|---|---|---|---|
| | Right Eye (Grade) | Left Eye (Grade) | Right Eye (Grade) | Left Eye (Grade) | Right Eye (Grade) | Left Eye (Grade) |
| Day 1 |  (2) |  (1-2) | 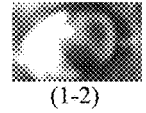 (1-2) |  (1-2) |  (1-2) |  (1-2) |
| Day 7 |  (about 1) | 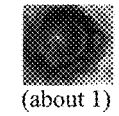 (about 1) |  (<1): | 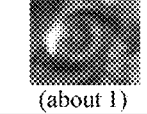 (about 1) | 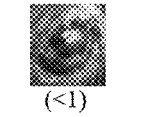 (<1) | 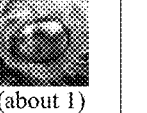 (about 1) |

COMPOSITIONS FOR THE TREATMENT OF CATARACTS

PRIORITY APPLICATIONS

This application incorporates the embodiments disclosed in U.S. Provisional Application No. 62/295,267, filed Feb. 15, 2016, U.S. Provisional Application No. 62/252,120, filed Nov. 6, 2015, U.S. Provisional Application No. 62/202,518 filed Aug. 7, 2015 and U.S. Provisional Application No. 62/197,477, filed Jul. 27, 2015, which are all incorporated herein by reference.

BACKGROUND OF THE INVENTION

Cataracts are the leading cause of blindness. Millions of patients every year undergo cataract surgery to remove the opacified lenses. Surgical treatment of cataracts, while effective, is not without risk of complications. It has been reported that congenital cataract is one of the common causes of visual impairment and childhood blindness. Congenital cataract occurs in an isolated fashion or as one component of a multi-system disorder. Nonsyndromic congenital cataracts have an estimated incidence of 1-6 per 10,000 live births. Nearly one-third of the cases show a positive family history, of which autosomal dominant inheritance is the most common. More than 20 genes have been identified responsible for isolated autosomal dominant congenital cataract. These genes encode crystallins, membrane transport proteins, cytoskeletal protein, and transcription factors. Crystallin proteins, including α-, β- and γ-crystallins, represent about 90% of lens soluble proteins in human. These proteins play critical roles in the optical transparency and high refractive index. α-Crystallins belong to the family of the small heat-shock proteins, acting as a molecular chaperone that protects proteins from misfolding. β- and γ-Crystallins, considered as a superfamily, are lens structural proteins and share a common two-domain structure, composed of four Greek-key motifs. γ-Crystallins include six members encoded by a gene cluster (CRYGA-F) on human chromosome 2. See Xiao-Qiao Li et al., Human Mutation, Research Article, Vol. 33, Issue 2, pp. 391-401, February 2012.

Zhao et al. (2015) The human lens is comprised largely of crystallin proteins assembled into a highly ordered, interactive macro-structure essential for lens transparency and refractive index. Any disruption of intra- or inter-protein interactions will alter this delicate structure, exposing hydrophobic surfaces, with consequent protein aggregation and cataract formation. Cataracts are the most common cause of blindness worldwide, affecting tens of millions of people, and currently the only treatment is surgical removal of cataractous lenses. The precise mechanisms by which lens proteins both prevent aggregation and maintain lens transparency are largely unknown. Lanosterol is an amphipathic molecule enriched in the lens. It is synthesized by lanosterol synthase (LSS) in a key cyclization reaction of a cholesterol synthesis pathway. Two distinct homozygous LSS missense mutations (W581R and G588S) in two families with extensive congenital cataracts. Both of these mutations affect highly conserved amino acid residues and impair key catalytic functions of LSS. Engineered expression of wild-type, but not mutant, LSS prevents intracellular protein aggregation of various cataract-causing mutant crystallins. Treatment by lanosterol, but not cholesterol, significantly decreased preformed protein aggregates both in vitro and in cell-transfection experiments. Zhao et al. have also demonstrated that lanosterol treatment could reduce cataract severity and increase transparency in dissected rabbit cataractous lenses in vitro and cataract severity in vivo in dogs. Zhao et al. identified lanosterol as an important compound in the prevention of lens protein aggregation and suggested a novel strategy for cataract prevention and treatment. See Ling Zhao et al., Lanosterol reverses protein aggregation in cataract, Nature, Research Letters, July, 2015. Similarly, Makley et al., Science, Vol. 350, Issue 6261, pp. 674-677, reported the administration of certain sterols as pharmacological chaperones for α-crystallin for partially restoring transparency in cataract models.

The foregoing examples of the related art and limitations are intended to be illustrative and not exclusive. Other limitations of the related art will become apparent to those of skill in the art upon a reading of the specification and a study of the drawings or figures as provided herein.

SUMMARY OF THE INVENTION

There is a need for effective non-invasive and non-surgical methods for the treatment of cataracts, including congenital cataracts. The present application dicloses novel formulations and methods for the prevention and treatment of cataracts. The following embodiments, aspects and variations thereof are exemplary and illustrative are not intended to be limiting in scope.

In one embodiment, the present application discloses compositions comprising a combination of steroids, such as lanosterol, and steroids that are formed downstream in the lanosterol or cholesterol biosynthetic pathway that are effective for the treatment of eye diseases, such as eye diseases, lesions and injuries, including cataracts. In another embodiment, the steroids include their prodrugs, such as their esters, including methyl esters and ethyl esters. In one embodiment, the mixture of steroids include lanosterol. In one variation of each of the embodiments, variations and aspects disclosed herein, the steroid formulation exclude lanosterol; and the steroid formulation exclude cholesterol as a single steroid.

In another embodiment, the present application discloses compositions comprising lanosterol that is effective for the treatment of eye diseases, such as lesions and injuries, including cataracts. In another embodiment, the lanosterol include the prodrugs, such as their esters, including methyl esters and ethyl esters.

In one embodiment, the present application discloses a method for the treatment of cataracts using the disclosed compositions or formulations. In one aspect, the present application discloses formulations and compositions, and methods for the treatment of cataracts, including the mutation of γC-crystallin in a patient with autosomal dominant congenital cataract.

In one embodiment, there is provided an aqueous ophthalmic composition for the treatment of eye diseases, lesions and injuries, comprising:

a) one steroid or a combination of at least two steroids selected from the group consisting of lanosterol, dihydrolanosterol, 4,4-dimethylcholesta-8(9), 14,24-trien-3β-ol, 4,4-dimethylcholesta-8,24-dien-3β-ol, 4,4-dimethylcholesta-8-en-3β-ol, 4,4-dimethylcholesta-8(9),14-dien-3β-ol, 14-desmethyl lanosterol, lathosterol, $\Delta^{7,24}$-cholestadienol, cholesterol, cholesta-7-enol, cholesteryl ester, 7-dehydrocholesterol, desmosterol (24-dehydrocholesterol), 7-dehydrodesmosterol, zymosterol, 27-hydroxycholesterol, cholesta-7,24-dien-3-β-ol, cholesta-8(9)-en-3-β-ol, 5α-cholestan-3β-ol-6-one, 5-cholesten-3β,25-diol, 5-cholesten-3β,25-OSO$_3$H (5-cholesten-3β,25-sulfate), 5-cholesten-3β-OSO₃H,25-ol (5-cholesten-3β-sulfate,25-ol), 5-cholesten-3β,25-diol, disulfate, and their esters thereof, or a pharmaceutically acceptable salt thereof, in a concentration effective for the treatment and/or prophylaxis of the eye diseases, lesions and injuries; and b) a pharmaceutical excipient.

In one variation of the above, the steroid is selected from the group consisting of 5α-cholestan-3β-ol-6-one, 5-cholesten-3β,25-diol, 5-cholesten-3β,25-OSO₃H (5-cholesten-3β,25-sulfate), 5-cholesten-3β-OSO₃H,25-ol (5-cholesten-3β-sulfate,25-ol) and 5-cholesten-3β,25-diol. In another variation, the combination or mixture of steroids is selected from the group consisting of 5α-cholestan-3β-ol-6-one, 5-cholesten-3β,25-diol, 5-cholesten-3β,25-OSO₃H (5-cholesten-3β,25-sulfate), 5-cholesten-3β-OSO₃H,25-ol (5-cholesten-3β-sulfate,25-ol) and 5-cholesten-3β,25-diol. In another variation, the mixture of two steroids is selected from 5α-cholestan-3β-ol-6-one and one steroid, or at least one steroid selected from the group consisting of 5-cholesten-3β,25-diol, 5-cholesten-3β,25-OSO₃H (5-cholesten-3β,25-sulfate), 5-cholesten-3β-OSO₃H,25-ol (5-cholesten-3β-sulfate,25-ol) and 5-cholesten-3β,25-diol.

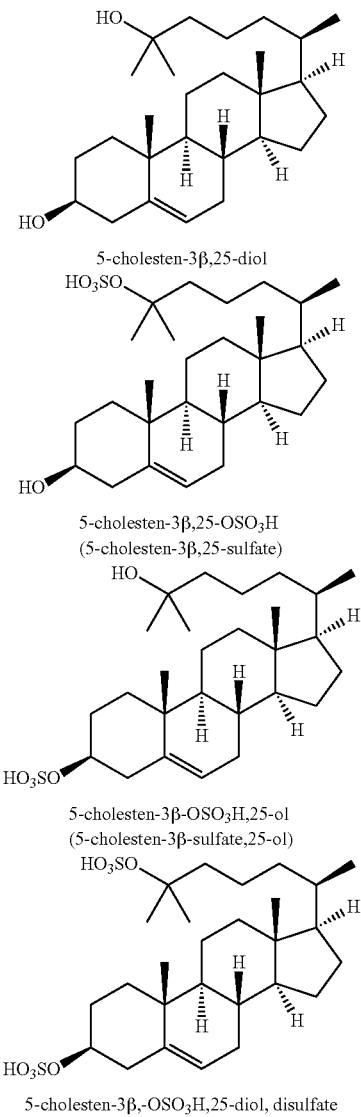

5-cholesten-3β,25-diol 5-cholesten-3β,25-OSO₃H
(5-cholesten-3β,25-sulfate)

5-cholesten-3β-OSO₃H,25-ol
(5-cholesten-3β-sulfate,25-ol)

5-cholesten-3β,-OSO₃H,25-diol, disulfate

In one variation, there is provided a pharmaceutical composition suitable for topical administration to an eye, comprising: (a) one steroid or at least two steroids selected from the group consisting of lanosterol, dihydrolanosterol, 4,4-dimethylcholesta-8(9), 14,24-trien-3β-ol, 4,4-dimethylcholesta-8,24-dien-3β-ol, 4,4-dimethylcholesta-8-en-3β-ol, 4,4-dimethylcholesta-8(9), 14-dien-3β-ol, 14-desmethyl lanosterol, lathosterol, Δ⁷,²⁴-cholestadienol, cholesterol, cholesta-7-enol, cholesteryl ester, 7-dehydrocholesterol, desmosterol (24-dehydrocholesterol), 7-dehydrodesmosterol, zymosterol, 27-hydroxycholesterol, cholesta-7,24-dien-3-β-ol, cholesta-8(9)-en-3-β-ol, 5α-cholestan-3β-ol-6-one, 5-cholesten-3β,25-diol, 5-cholesten-3β,25-OSO₃H (5-cholesten-3β,25-sulfate), 5-cholesten-3β-OSO₃H,25-ol (5-cholesten-3β-sulfate,25-ol), 5-cholesten-3β,25-diol, disulfate, or a pharmaceutically acceptable salt thereof in a concentration effective for treatment and/or prophylaxis of the eye diseases, lesions and injuries; (b) a pharmaceutically acceptable cyclodextrin compound in a cyclodextrin concentration sufficient to maintain the steroids in solution; and (c) at least one or at least two ophthalmically compatible polymers selected from the group consisting of konjac and sodium alginate; konjac and hydroxy propyl guar; konjac and propylene glycol alginate; konjac and Carbopol 971; hydroxy propyl guar and agarose; propylene glycol alginate and agarose; and propylene glycol alginate and scleroglucan. In one variation of the above, the steroid is selected from the group consisting of 5α-cholestan-3β-ol-6-one, 5-cholesten-3β,25-diol, 5-cholesten-3β,25-OSO₃H (5-cholesten-3β,25-sulfate), 5-cholesten-3β-OSO₃H,25-ol (5-cholesten-3β-sulfate,25-ol) and 5-cholesten-3β,25-diol. In another variation, the combination or mixture of steroids, or the at least two steroids is selected from the group consisting of 5α-cholestan-3β-ol-6-one, 5-cholesten-3β,25-diol, 5-cholesten-3β,25-OSO₃H (5-cholesten-3β,25-sulfate), 5-cholesten-3β-OSO₃H,25-ol (5-cholesten-3β-sulfate,25-ol) and 5-cholesten-3β,25-diol. In another variation, the mixture of two steroids is selected from 5α-cholestan-3β-ol-6-one and one steroid selected from the group consisting of 5-cholesten-3β,25-diol, 5-cholesten-3β,25-OSO₃H (5-cholesten-3β,25-sulfate), 5-cholesten-3β-OSO₃H,25-ol (5-cholesten-3β-sulfate,25-ol) and 5-cholesten-3β,25-diol.

In one variation of the above composition or formulation, lanosterol is present as a component of the composition. In another variation, lanosterol is present as the only steroid in the composition or formulation. In another variation of the composition, lanosterol is present at a concentration of at least 50%, at least 60%, at least 70%, at least 80%, at least 90% and at least 95% of the steroids mixture. In another variation of the composition, the concentration of the steroid in the composition is about 1 to 100 mM, 1 to 75 mM, 1 to 50 mM, 1 to 25 mM, or 1 to 10 mM. In another variation, the concentration of the steroid in the composition is about 50 to 100 mM, 75 to 100 mM, 85 to 100 mM, or 90 to 100 mM. In another variation, the concentration of the steroid in the composition is about 25 to 75 mM, 35 to 65 mM, or about 45 to 55 mM.

In one variation of the above, the composition or formulation is a topical pharmaceutical formulation. In one aspect, the present formulations overcome one of the major problems encountered with topical delivery of ophthalmic drugs that is the rapid and extensive precorneal loss due to drainage and high tear fluid turnover.

In another aspect of the composition, the eye disease is cataract. In another aspect, the composition further comprises at least one cellulose selected from a group consisting of carboxymethylcellulose, hydroxyethylcellulose and hydroxypropylmethylcellulose, a pharmacologically acceptable salt thereof, or a mixture thereof. In another variation, the formulation further comprises carboxypolymethylene or polyvinylpyrrolidone.

In one variation, the composition is suitable for topical administration to the eye. In another variation, the amount of the carboxypolymethylene or polyvinylpyrrolidone is effective to increase the intraocular absorption of the steroid, for example, in the eye and/or in the aqueous humor.

In yet another variation, the formulation comprises a cyclodextrin compound in a concentration sufficient to ensure that essentially all of the steroid agent in the composition is in solution. In one aspect, the cyclodextrin compound is selected from the group consisting of α-cyclodextrin, β-cyclodextrin, λ-cyclodextrin, an alkylcyclodextrin, a hydroxyalkylcyclodextrin, a carboxyalkyl-cyclodextrin, and sulfoalkylether cyclodextrin. In another variation, the cyclodextrin compound is selected from the group consisting of hydroxypropyl-β-cyclodextrin and sulfobutylether-β-cyclodextrin. In one variation of the above, the cyclodextrin concentration is about 1 mg/ml to about 500 mg/ml, 10 mg/ml to about 400 mg/ml, 100 mg/ml to about 300 mg/ml or 150 mg/ml to about 250 mg/ml. In another variation, the cyclodextrin concentration is about 1 mg/ml to about 250 mg/ml, 1 mg/ml to about 200 mg/ml, 1 mg/ml to about 150 mg/ml or 1 mg/ml to about 100 mg/ml.

In another aspect of the above composition, the total concentration of the steroids in the composition is about 0.001 to 1.0 mg/ml. In another aspect, the composition provides a dose range of the steroids at about 0.01 to about 100 mg/kg/day.

In one variation of the above composition, the dose range is 0.1 to about 100 mg/kg/day. In another variation, the dose range is 0.1 to 50 mg/kg/day, 0.1 to 25 mg/kg/day, 0.1 to 20 mg/kg/day, 0.1 to 15 mg/kg/day, or 0.1 to 10 mg/kg/day. In another variation, the dose range is 50 to 100 mg/kg/day, 60 to 100 mg/kg/day, 75 to 100 mg/kg/day, 85 to 100 mg/kg/day, 90 to 100 mg/kg/day, or 95 to 100 mg/kg/day. In another variation, the dose range is 25 to 75 mg/kg/day, 30 to 75 mg/kg/day, 45 to 75 mg/kg/day, 50 to 75 mg/kg/day, 60 to 75 mg/kg/day, or 65 to 75 mg/kg/day.

In another aspect of the composition, the amount of the steroid in the composition is in the range of 0.0005% to 0.5% wt/wt, 0.001% to 0.5% wt/wt, 0.01% to 0.5% wt/wt or 0.1% to 0.5% wt/wt. In another aspect of the composition, the amount of the cellulose is about 0.01% to 0.5%. In one variation of the composition, the amount of the cellulose is about 0.2% to 0.4%, 0.25% to 0.35% or about 0.3%. In one variation of the above, the composition is a steroid formulation (100 mg)-loaded nanoparticles. In another variation, the steroid formulation in the nanoparticles is 0.01 to 100 mg, 0.01 to 50 mg, 0.01 to 25 mg, 0.01 to 10 mg or 0.01 to 1 mg.

In another aspect of the above, the composition further comprises a preservative selected from benzyl alcohol or para-amino-benzoic acid. In another aspect, the composition of the steroids or the ratio of the steroids are as disclosed in Tables 1 to 8, as disclosed herein. In another aspect, the above composition further comprises a lubricant which is acceptable for topical administration to the eye. In another aspect, the composition is suitable for daily administration to the eye. In yet another aspect of the above composition, the composition is suitable for administration daily for at least 1 week.

In one variation, the composition comprises a therapeutically effective amount of the steroid, and a pharmaceutically acceptable excipient. In one aspect the above, the composition is suitable for daily administration to the eye.

In one variation, the composition may be administered daily, every 2 days, every 3 days, every 4 days, every 5 days, or weekly for at least one week; or the composition may be administered at least 2 weeks, at least 3 weeks or at least 4 weeks or more. In another variation, the composition may be administered accordingly, at least once a day or at least twice a day for the above noted period of time. In another variation, the composition is suitable for administration topically twice daily for 4 weeks or more. In another variation, the composition is suitable for administration topically for 6 months or more.

In another variation, the composition is suitable for use as a medicament to treat eye diseases, lesions and injuries, and wherein the composition is suitable for administration in combination with other eye medications.

In another aspect of the above, the composition may be administered daily, every 2 days, every 3 days, every 4 days, every 5 days, or weekly for at least one week.

In another embodiment, there is provided a method for the treatment of eye diseases, lesions and injuries, the method comprising an administration of a composition comprising: a) one steroid or a combination of at least two steroids selected from the group consisting of lanosterol, dihydrolanosterol, 4,4-dimethylcholesta-8 (9), 14,24-trien-3β-ol, 4,4-dimethylcholesta-8,24-dien-3β-ol, 4,4-dimethylcholesta-8-en-3β-ol, 4,4-dimethylcholesta-8(9),14-dien-3β-ol, 14-desmethyl lanosterol, lathosterol, $\Delta^{7,24}$-cholestadienol, cholesterol, cholesta-7-enol, cholesteryl ester, 7-dehydrocholesterol, desmosterol (24-dehydrocholesterol), 7-dehydrodesmosterol, zymosterol, 27-hydroxycholesterol, cholesta-7, 24-dien-3-β-ol, cholesta-8(9)-en-3-β-ol, 5α-cholestan-3β-ol-6-one, 5-cholesten-3β,25-diol, 5-cholesten-3β, 25-$OSO_3H$ (5-cholesten-3β,25-sulfate), 5-cholesten-3β-$OSO_3H$,25-ol (5-cholesten-3β-sulfate,25-ol), 5-cholesten-3β,25-diol, disulfate, and their esters thereof, or a pharmaceutically acceptable salt thereof, in a concentration effective for the treatment and/or prophylaxis of the eye diseases, lesions and injuries; and b) a pharmaceutical excipient; to a patient in need thereof.

In one aspect of the above method, the eye disease is cataracts. In another aspect of the method, the administration is effective to prevent the formation of cataracts or effective to treat cataracts. In another aspect of the above method, the administration of the composition reverses protein aggregation in cataracts or significantly reduces the severity of the cataract and increases the lens clarity.

In another aspect of the above method, the administration of the composition significantly inhibits aggresome formation of both wild-type and mutated crystalline proteins.

In one variation of the above, the methods reverse cataracts in the patient. In one variation of the above, the methods are effective in at least one of suppressing, partially suppressing or partially reversing amyloid formation. In another aspect, the disclosed methods block aggregation and reverse or partially reverse R120G cryAB (αβ-crystallin), cryAB and cryAA insolubility in the protein content of a lens. In another aspect, the methods bind and stabilize crystallins. In another aspect, the methods stabilize the soluble forms of cryAB and suppress its aggregation. In another aspect, the disclosed methods is effective in a number of ways, including restoring protein solubility; improving the solubility of the α-crystallins, including cryAA and cryAB; improving transparency as determined by at least one grade on the LOCS III scoring system; reversing protein aggregation by binding and stabilizing the more soluble forms of cryAA and cryAB; and stabilizing the native forms of cryAB. The above methods are effective by at least 20%, at least 30%, at least 40%, at least 50%, at least 70%, at least 80% at least 90% or at least 95%. In one variation, the method reduces the severity of the cataract by at least 50%, at least 70%, at least 80% at least 90% or at least 95%. In another variation, the administration of the composition to the eye results in the release of mutant crystalline proteins from aggregation. In another variation, the administration of the composition re-dissolves the aggregated crystallin proteins from the amyloid-like fibrils in the lens tissues of the eye. In another variation, the administration is effective to reduce intraocular pressure on chronic topical ocular and of primary open-angle glaucoma and ocular hypertension.

In another aspect of the above methods, the composition may be administered to patients with primary open-angle glaucoma-, ocular hypertension with accompanying cataracts.

In another embodiment, there is provided a method for inhibiting lens protein aggregation, treating cataract, reducing cataract formation, reducing cataract severity and increased lens clarity comprising the administration of a composition of any of the above compositions and as disclosed herein.

In another embodiment, there is provided a method for decreasing protein aggregation caused by mutant crystallin proteins culture and reducing preformed cataract severity by increasing lens clarity, the method comprising the administration of a composition of any one of any one of the above, and as disclosed herein. In one aspect of the above method, the therapeutically effective amount is effective to treat cataract. In another aspect of the above methods, the administration is a topical administration.

In one variation, the therapeutically effective amount is effective to inhibiting lens protein aggregation, treating cataract, reducing cataract formation, reducing cataract severity and increased lens clarity. In another variation of the above method, the method comprise administering a pharmaceutically effective amount of the steroids to a patient in need of treatment, wherein a pharmaceutically effective amount of the steroid comprises an amount sufficient to ameliorate the disease.

In one embodiment, the pharmacologically acceptable salts of cellulose include carboxymethylcellulose sodium and sodium cellulose glycolate. The USP describes carboxymethylcellulose sodium as the sodium salt of a polycarboxymethyl ether of cellulose. A typical molecular weight for the cellulose is 90,000-700,000. Cellulose compounds suitable for use in the present formulation are commercially available in various forms from various manufacturers. Benzene-free carboxypolymethylene is commercially available under the trademark CARBOMER 980. Polyvinylpyrrolidone is commercially available under the trademark KOLLIDON K17. In one variation of each of the embodiments, variations and aspects disclosed herein, the steroid formulations exclude lanosterol.

In another embodiment, the formulation comprises at least one, or at least two ophthalmically compatible compounds and polymers selected from the group consisting of konjac and sodium alginate; konjac and hydroxy propyl guar; konjac and propylene glycol alginate; konjac and Carbopol 971; hydroxy propyl guar and agarose; propylene glycol alginate and agarose; and propylene glycol alginate and scleroglucan.

Also included in the above embodiments, aspects and variations are salts of amino acids such as arginate and the like, gluconate, and galacturonate. Some of the compounds of the invention may form inner salts or Zwitterions. Certain of the compounds of the present invention can exist in unsolvated forms as well as solvated forms, including hydrated forms, and are intended to be within the scope of the present invention. Certain of the above compounds may also exist in one or more solid or crystalline phases or polymorphs, the variable biological activities of such polymorphs or mixtures of such polymorphs are also included in the scope of this invention. Also provided are pharmaceutical compositions comprising pharmaceutically acceptable excipients and a therapeutically effective amount of at least one compound of this invention.

Pharmaceutical compositions of the compounds of this invention, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration but may also be used for oral administration. Excipients, such as polyvinylpyrrolidinone, gelatin, hydroxycellulose, acacia, polyethylene glycol, mannitol, sodium chloride, or sodium citrate, may also be added. Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols or water. Solid carriers include starch, lactose, calcium sulfate, dihydrate, terra alba, magnesium stearate or stearic acid, talc, pectin, acacia, agar, or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulation, and compressing, when necessary, for tablet forms; or milling, mixing, and filling for hard gelatin capsule forms. When a liquid carrier is used, the preparation will be in the form of a syrup, elixir, emulsion, or an aqueous or non-aqueous suspension. Such a liquid formulation may be administered directly p.o. or filled into a soft gelatin capsule. Suitable formulations for each of these methods of administration may be found in, for example, *Remington: The Science and Practice of Pharmacy*, A. Gennaro, ed., 20th edition, Lippincott, Williams & Wilkins, Philadelphia, Pa.

In one variation, there is provided the above steroids, or a pharmaceutically acceptable salts thereof, and as applicable with respect to their possible isomers, in the form of a single stereoisomer or mixture of stereoisomers thereof.

In addition to the exemplary embodiments, aspects and variations described above, further embodiments, aspects and variations will become apparent by reference to the tables and figures and by examination of the following descriptions.

DETAILED DESCRIPTION OF THE INVENTION

Definitions

Unless specifically noted otherwise herein, the definitions of the terms used are standard definitions used in the art of organic synthesis and pharmaceutical sciences. Exemplary embodiments, aspects and variations are illustrative in the figures and drawings, and it is intended that the embodiments, aspects and variations, and the figures and drawings disclosed herein are to be considered illustrative and not limiting.

Mammals that may be treated according to the methods of the present application include humans, canines (dogs), cats, rabbits and equines.

By "eye diseases" it is meant eye disorders including cataract, open-angle primary glaucoma, corneal disorders, presbyopia, computer vision syndrome, eye strain, ocular inflammation, blurred vision, dry eye syndrome, retinal diseases, vitreous opacities and lesions, complications of diabetes mellitus and other systemic diseases. In one embodiment, the eye disease is cataract.

The term "gum", refers to any synthetic or non-synthetic polymer, natural polysaccharide, or derivatized natural polysaccharide that is ophthalmically compatible and that increases the viscosity of a solution or formulation sufficiently to increase the viscosity of the solution or formulation in which it is found or to transform a drop of the solution into a semi-solid or gelatinous state after administration to an eye of a patient. Non-exclusive examples of synthetic polymer gums include polyethylene glycol, polyvinyl pyrrolidone, carboxymethyl cellulose, polyvinyl alcohol and derivatives thereof, and Carbopol and derivatives thereof. Non-exclusive examples of natural polysaccharide gums include carrageenan, konjac, sodium alginate, aloe vera gel, agarose, guar, pectin, tragacanth, acacia, Arabic, curdlan, gellan, xanthan, scleroglucan, hyaluronic acid, or chitosan. Non-exclusive examples of derivatized natural polysaccharide gums include propyleneglycol alginate and hydroxypropyl guar.

The clause "ophthalmic composition" or "ophthalmic formulation" refers to a composition for application to the eye or its related or surrounding tissues such as, for example, the eyelid. The term also includes compositions for treating conditions of the eye itself or the tissues surrounding the eye. The ophthalmic composition can be applied topically or by other techniques, known to persons skilled in the art, such as injection to the eye or its related tissues. Examples of suitable topical administration to the eye include administration in eye drops and by spray formulations. A further suitable topical administration route is by subconjunctival injection. The formulations may also be provided to the eye periocularly or retro-orbitally. In certain embodiments, intracameral administration may be employed.

The clause "flowable mucoadhesive polymer" refers to a carboxy-containing polymer, for example, lightly cross-linked polymers of acrylic acid or the like, having an optimal in vivo mucosal absorption rate, safety, degradability and flowability for an eye drop. The flowable mucoadhesive polymers used in the present application are water insoluble, water-swellable, biodegradable polymer carriers including lightly crosslinked carboxy-containing polymers such as polycarbophil (Noveon™ AA-1, Lubizol Corp., Wickliffe, Ohio) or other Carbopol™ polymers (Lubizol Corp., Wickliffe, Ohio). Suitable carboxy-containing polymers for use in the present invention and methods for making them are described in U.S. Pat. No. 5,192,535. A suitable carboxy-containing polymer system for use in the present application include DuraSite™ (InSite Vision Inc., Alameda, Calif.), containing polycarbophil, which is a sustained release topical ophthalmic delivery system that releases drug at a controlled rate. The polymer systems include lightly cross-linked polymers that are prepared by suspension or emulsion polymerizing at least about 90% by weight of a carboxyl-containing mono-ethylenically unsaturated monomer such as acrylic acid with from about 0.1% to about 5% by weight of a polyfunctional, or difunctional, crosslinking agent such as divinyl glycol (3,4-dihydroxy-1,5-hexadiene), having a particle size of not more than about 50 µm in equivalent spherical diameter, when formulated with an ophthalmic medicament, such as the steroid formulation, into solutions or suspensions in aqueous medium in which the amount of polymer ranges from about 0.5% to about 1.5% by weight, based on the total weight of the aqueous suspension. In one embodiment, the pH is from about 7.4 to about 8.5, and the osmotic pressure (osmolality or tonicity) is from about 10 mOsM to about 400 mOsM, provide a topical ophthalmic medicament delivery systems having suitably low viscosities for administration to the eye in drop form. These formulations may rapidly gel in the eye after coming into contact with the eye's tear fluid to a substantially greater viscosity than that of the originally-introduced suspension or solution and thus remain in place for prolonged periods of time to provide sustained release of the ophthalmic medicament.

"Pharmaceutically acceptable salts" means salt compositions that is generally considered to have the desired pharmacological activity, is considered to be safe, non-toxic and is acceptable for veterinary and human pharmaceutical applications. Such salts include acid addition salts formed with inorganic acids such as hydrochloric acid, hydrobromic acid, sulfuric acid, phosphoric acid, and the like; or with organic acids such as acetic acid, propionic acid, hexanoic acid, malonic acid, succinic acid, malic acid, citric acid, gluconic acid, salicylic acid and the like.

The clause "sustained release delivery system" or "sustained release composition" refers to a formulation or composition comprising a flowable mucoadhesive polymer, which may be a carboxy-containing polymer such as polycarbophil and DuraSite™, as described in U.S. Pat. No. 5,192,535, that facilitates a sustained release of the steroid formulation. The sustained release delivery systems, formulations or compositions may be prepared in many forms or shapes, such as a solution, a gel, a film, a pellet, a rod, a filament, a cylinder, a disc, a wafer, nanoparticles or a microparticle. A "microparticle" as defined herein, comprises a blend polymer component having a diameter of less than about one millimeter and having the steroid formulation dispersed therein. A microparticle can have a spherical, non-spherical or irregular shape. In one aspect, the microparticle will be of a size suitable for injection. In another aspect, the size range for microparticles is from about one to about 50 microns in diameter.

The clause "steroid formulation" or "steroids formulation" as used herein may include a single steroid that is lanosterol, or may include at least two steroids comprising lanosterol and a second steroid disclosed herein. In another embodiment, the term "steroid formulation" may include a single steroid that is not lanosterol, or at least two steroids disclosed in the specification, such as the compounds or steroids in Tables 1 to 9.

"Therapeutically effective amount" means an amount of the steroids that elicit any of the biological effects listed in the specification.

The term "treating" or "treatment" refers to reducing, ameliorating reversing, alleviating, inhibiting the progress of, or preventing a disease or a medical condition of the eye itself or the tissue surrounding the eye or the symptoms associated therewith. The term also encompasses prophylaxis, therapy and cure. The subject or patient receiving "treatment," or whom undergoes "treating" is any mammal in need of such treatment for (eye-related diseases, such as cataracts, inflammation or inflammatory conditions, or combinations thereof), including primates, in such as humans, and other mammals such as equines, cattle, swine and sheep; and domesticated mammals and pets in general.

BRIEF DESCRIPTION OF THE FIGURE

FIG. 1 shows some representative results for the administration of the formulations that provided at least 5% to 20% percent improvement in the clarity of the lens, restoring protein solubility, improving solubility of the α-crystallins, improving transparency and reversing protein aggregation.

The following Tables provide illustrative representations of different formulations with a variation in the ratio of the steroids that may be used in the formulation. In one aspect, the total amount of the steroids in the composition may be in the range of 0.0005% to 0.5% wt/wt, 0.0005% to 0.2% wt/wt, 0.0005% to 0.1% wt/wt or as disclosed herein.

TABLE 1

| Steroids | Formulation Numbers Ratio of Steroids by % wt/wt | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Lanosterol | 95 | 95 | 95 | 95 | 95 | 95 | 95 | 95 | 95 | 95 | 95 | 95 | 95 | 95 | 95 |
| Dihydrolanosterol | 2 | 2 | 1 | 1 | 1 | — | — | — | — | — | — | — | — | — | — |
| 4,4-Dimethylcholesta-8(9),14,24-trien-3β-ol | 2 | 1 | 1 | 1 | 1 | 1 | 2 | 2 | 2 | 2 | 1 | 1 | 1 | 1 | — |
| 4,4-Dimethylcholesta-8,24-dien-3β-ol | 1 | 1 | 1 | — | — | 1 | 1 | 1 | — | — | 1 | 1 | 1 | 1 | — |
| 4,4-Dimethylcholesta-8(9),14-dien-3β-ol | — | — | — | — | — | — | — | — | 1 | — | — | — | 1 | 1 | 2 |
| 4,4-Dimethylcholesta-8-en-3β-ol | — | — | — | — | — | — | — | — | 1 | 2 | — | — | 1 | — | 1 |
| 14-Desmethyl lanosterol | — | — | — | — | — | — | — | — | — | — | — | — | — | — | — |
| Lathosterol | — | — | — | — | 1 | — | — | — | — | — | — | — | — | — | 1 |
| $\Delta^{7,24}$-Cholestadienol | — | 1 | 1 | 1 | — | 1 | 1 | — | 1 | 1 | 1 | 2 | 1 | — | 1 |
| Cholesterol | — | — | — | — | — | — | — | — | — | — | — | — | — | — | — |
| Cholesta-7-enol | — | — | — | — | — | — | — | — | — | — | — | — | — | — | — |
| Cholesteryl ester | — | — | — | — | — | — | — | — | — | — | — | — | — | — | — |
| 7-Dehydrocholesterol | — | — | — | — | — | — | — | — | — | — | — | — | — | — | — |
| Desmosterol (24-dehydrocholesterol) | — | — | — | 1 | 1 | 1 | 1 | 1 | — | — | 1 | 1 | — | 1 | — |
| 7-Dehydrodesmosterol | — | — | — | — | — | — | — | — | — | — | — | — | — | — | — |
| Zymosterol | — | — | 1 | 1 | 1 | 1 | — | 1 | — | — | 1 | — | — | 1 | — |
| 27-Hydroxycholesterol | — | — | — | — | — | — | — | — | — | — | — | — | — | — | — |
| Cholesta-7,24-dien-3-β-ol | — | — | — | — | — | — | — | — | — | — | — | — | — | — | — |
| Cholesta-8(9)-en-3-β-ol | — | — | — | — | — | — | — | — | — | — | — | — | — | — | — |

—Means none added to formulation.

TABLE 2

| Steroids | Formulation Numbers Ratio of Steroids by % wt/wt | | | | | | | | | | | | | | |
|---|---|---|---|---|---|---|---|---|---|---|---|---|---|---|---|
| | 16 | 17 | 18 | 19 | 20 | 21 | 22 | 23 | 24 | 25 | 26 | 27 | 28 | 29 | 30 |
| Lanosterol | 90 | 90 | 90 | 90 | 90 | 90 | 90 | 90 | 90 | 90 | 90 | 90 | 90 | 90 | 90 |
| Dihydrolanosterol | 5 | 5 | 5 | 5 | 5 | — | — | — | — | — | — | — | — | — | — |
| 4,4-Dimethylcholesta-8(9),14,24-trien-3β-ol | 5 | 3 | 2 | 2 | 1 | 5 | 5 | 5 | 5 | 5 | 7 | 7 | 7 | 7 | — |
| 4,4-Dimethylcholesta-8,24-dien-3β-ol | — | 1 | 1 | — | — | 2 | 1 | 1 | — | — | 1 | 1 | — | 1 | — |
| 4,4-Dimethylcholesta-8(9),14-dien-3β-ol | — | — | — | — | — | — | — | — | 3 | — | — | — | 1 | 1 | 7 |
| 4,4-Dimethylcholesta-8-en-3β-ol | — | — | — | — | — | — | — | — | 1 | 2 | — | — | 1 | — | 1 |
| 14-Desmethyl lanosterol | — | — | — | — | — | — | — | — | — | — | — | — | — | — | — |
| Lathosterol | — | — | — | — | 1 | — | — | — | — | — | — | — | — | — | 1 |
| $\Delta^{7,24}$-Cholestadienol | — | 1 | 1 | 1 | — | 1 | 3 | — | 1 | 1 | 1 | 2 | — | — | 1 |
| Cholesterol | — | — | — | — | 1 | — | — | — | — | — | — | — | — | — | — |
| Cholesta-7-enol | — | — | — | — | — | — | — | — | — | — | — | — | — | — | — |
| Cholesteryl ester | — | — | — | — | — | — | — | — | — | — | — | — | — | — | — |
| 7-Dehydrocholesterol | — | — | — | — | — | — | — | — | — | — | — | — | — | — | — |
| Desmosterol (24-dehydrocholesterol) | — | — | — | 1 | 1 | 1 | 1 | 2 | — | 1 | 1 | — | 1 | 1 | — |

TABLE 2-continued

| Steroids | Formulation Numbers Ratio of Steroids by % wt/wt | | | | | | | | | | | | | | |
|---|---|---|---|---|---|---|---|---|---|---|---|---|---|---|---|
| | 16 | 17 | 18 | 19 | 20 | 21 | 22 | 23 | 24 | 25 | 26 | 27 | 28 | 29 | 30 |
| 7-Dehydrodesmosterol | — | — | — | — | — | — | — | — | — | — | — | — | — | — | — |
| Zymosterol | — | — | 1 | 1 | 1 | 1 | — | 2 | — | 1 | — | — | — | — | — |
| 27-Hydroxycholesterol | — | — | — | — | — | — | — | — | — | — | — | — | — | — | — |
| Cholesta-7,24-dien-3-β-ol | — | — | — | — | — | — | — | — | — | — | — | — | — | — | — |
| Cholesta-8(9)-en-3-β-ol | — | — | — | — | — | — | — | — | — | — | — | — | — | — | — |

—Means none added to formulation.

TABLE 3

| Steroids | Formulation Numbers Ratio of Steroids by % wt/wt | | | | | | | | | | | | | | |
|---|---|---|---|---|---|---|---|---|---|---|---|---|---|---|---|
| | 31 | 32 | 33 | 34 | 35 | 36 | 37 | 38 | 39 | 40 | 41 | 42 | 43 | 44 | 45 |
| Lanosterol | 80 | 80 | 80 | 80 | 80 | 80 | 80 | 80 | 80 | 80 | 80 | 80 | 80 | 80 | 80 |
| Dihydrolanosterol | 10 | 10 | 10 | 10 | 10 | — | — | — | — | — | — | — | — | — | — |
| 4,4-Dimethylcholesta-8(9),14,24-trien-3β-ol | 10 | 3 | 5 | 5 | 5 | 10 | 10 | 10 | 10 | 10 | 15 | 15 | 15 | 15 | — |
| 4,4-Dimethylcholesta-8,24-dien-3β-ol | — | 3 | 1 | — | — | 5 | 1 | 1 | — | — | 1 | 1 | — | 3 | — |
| 4,4-Dimethylcholesta-8(9),14-dien-3β-ol | — | — | — | — | — | — | — | — | 3 | — | — | — | 2 | 1 | 15 |
| 4,4-Dimethylcholesta-8-en-3β-ol | — | — | — | — | — | — | — | — | — | 4 | 5 | — | — | 1 | — | 1 |
| 14-Desmethyl lanosterol | — | — | — | — | — | — | — | — | — | — | — | — | — | — | — |
| Lathosterol | — | — | — | — | 1 | — | — | — | — | — | — | — | — | — | 1 |
| Δ$^{7,24}$-Cholestadienol | — | 1 | 2 | 2 | 1 | 1 | 5 | — | 3 | 2 | 1 | 2 | — | — | 1 |
| Cholesterol | — | — | — | — | 1 | — | — | — | — | — | — | — | — | — | — |
| Cholesta-7-enol | — | — | — | — | — | — | — | — | — | — | — | — | — | — | — |
| Cholesteryl ester | — | — | — | — | — | — | — | — | — | — | — | — | — | — | — |
| 7-Dehydrocholesterol | — | — | — | — | — | — | — | — | — | — | — | — | — | — | — |
| Desmosterol (24-dehydrocholesterol) | — | 1 | — | 1 | 1 | 2 | 4 | 5 | — | 2 | 1 | — | 2 | 1 | — |
| 7-Dehydrodesmosterol | — | — | — | — | — | — | — | — | — | — | — | — | — | — | — |
| Zymosterol | — | 2 | 2 | 2 | 1 | 2 | — | 4 | — | 1 | 2 | 2 | — | — | 2 |
| 27-Hydroxycholesterol | — | — | — | — | — | — | — | — | — | — | — | — | — | — | — |
| Cholesta-7,24-dien-3-β-ol | — | — | — | — | — | — | — | — | — | — | — | — | — | — | — |
| Cholesta-8(9)-en-3-β-ol | — | — | — | — | — | — | — | — | — | — | — | — | — | — | — |

—Means none added to formulation.

TABLE 4

| Steroids | Formulation Numbers Ratio of Steroids by % wt/wt | | | | | | | | | | | | | | |
|---|---|---|---|---|---|---|---|---|---|---|---|---|---|---|---|
| | 46 | 47 | 48 | 49 | 50 | 51 | 52 | 53 | 54 | 55 | 56 | 57 | 58 | 59 | 60 |
| Lanosterol | 70 | 70 | 70 | 70 | 70 | 70 | 70 | 70 | 70 | 70 | 70 | 70 | 70 | 70 | 70 |
| Dihydrolanosterol | 10 | 10 | 10 | 10 | 10 | — | — | — | — | — | — | — | — | — | — |
| 4,4-Dimethylcholesta-8(9),14,24-trien-3β-ol | 10 | 5 | 5 | 5 | 5 | 20 | 20 | 20 | 20 | 20 | 15 | 15 | 15 | 15 | — |
| 4,4-Dimethylcholesta-8,24-dien-3β-ol | 10 | 5 | 5 | — | — | 3 | 1 | 1 | — | — | 10 | 1 | — | 5 | — |
| 4,4-Dimethylcholesta-8(9),14-dien-3β-ol | — | — | — | — | — | — | — | — | 5 | — | — | — | 10 | 3 | 15 |
| 4,4-Dimethylcholesta-8-en-3β-ol | — | — | — | — | — | — | — | — | 2 | 5 | — | — | 1 | — | 1 |
| 14-Desmethyl lanosterol | — | — | — | — | — | — | — | — | — | — | — | — | — | — | — |
| Lathosterol | — | — | — | — | 5 | — | — | — | — | — | — | — | — | — | 1 |
| Δ$^{7,24}$-Cholestadienol | — | 5 | 5 | 5 | 5 | 3 | 5 | — | 3 | 2 | 1 | 4 | — | — | 1 |
| Cholesterol | — | — | — | — | 3 | — | — | — | — | — | — | — | — | — | — |
| Cholesta-7-enol | — | — | — | — | — | — | — | — | — | — | — | — | — | — | — |
| Cholesteryl ester | — | — | — | — | — | — | — | — | — | — | — | — | — | — | — |
| 7-Dehydrocholesterol | — | — | — | — | — | — | — | — | — | — | — | — | — | — | — |
| Desmosterol (24-dehydrocholesterol) | — | 5 | — | 5 | 1 | 2 | 4 | 4 | — | 2 | 1 | — | 2 | 2 | — |

TABLE 4-continued

| Steroids | \multicolumn{15}{c}{Formulation Numbers<br>Ratio of Steroids by % wt/wt} |
|---|---|---|---|---|---|---|---|---|---|---|---|---|---|---|---|
|  | 46 | 47 | 48 | 49 | 50 | 51 | 52 | 53 | 54 | 55 | 56 | 57 | 58 | 59 | 60 |
| 7-Dehydrodesmosterol | — | — | — | — | — | — | — | — | — | — | — | — | — | — | — |
| Zymosterol | — | — | 5 | 5 | 1 | 2 | — | 5 | — | 1 | 3 | 10 | 2 | 5 | 2 |
| 27-Hydroxycholesterol | — | — | — | — | — | — | — | — | — | — | — | — | — | — | — |
| Cholesta-7,24-dien-3-β-ol | — | — | — | — | — | — | — | — | — | — | — | — | — | — | — |
| Cholesta-8(9)-en-3-β-ol | — | — | — | — | — | — | — | — | — | — | — | — | — | — | — |

—Means none added to formulation.

TABLE 5

| Steroids | Formulation Numbers<br>Ratio of Steroids by % wt/wt | | | | | | | | | | | | | | |
|---|---|---|---|---|---|---|---|---|---|---|---|---|---|---|---|
|  | 61 | 62 | 63 | 64 | 65 | 66 | 67 | 68 | 69 | 70 | 71 | 72 | 73 | 74 | 75 |
| Lanosterol | 60 | 60 | 60 | 60 | 60 | 60 | 60 | 60 | 50 | 50 | 50 | 50 | 50 | 50 | 50 |
| Dihydrolanosterol | 20 | 20 | 20 | 20 | 20 | — | — | — | — | — | — | — | — | — | — |
| 4,4-Dimethylcholesta-8(9),14,24-trien-3β-ol | 10 | 5 | 5 | 5 | 5 | 20 | 20 | 20 | 30 | 30 | 30 | 15 | 15 | 15 | — |
| 4,4-Dimethylcholesta-8,24-dien-3β-ol | 10 | 5 | 5 | — | — | 3 | 1 | 1 | — | — | 10 | 1 | — | 5 | — |
| 4,4-Dimethylcholesta-8(9),14-dien-3β-ol | — | — | — | — | — | — | — | — | — | 10 | — | — | 20 | 3 | 25 |
| 4,4-Dimethylcholesta-8-en-3β-ol | — | — | — | — | — | — | — | — | 5 | 5 | — | — | 1 | — | 1 |
| 14-Desmethyl lanosterol | — | — | — | — | — | — | — | — | — | — | — | — | — | — | — |
| Lathosterol | — | — | — | — | 5 | — | — | — | — | — | — | — | — | — | 1 |
| $\Delta^{7,24}$-Cholestadienol | — | 5 | 5 | 5 | 5 | 3 | 5 | — | 5 | 5 | 1 | 4 | — | — | 1 |
| Cholesterol | — | — | — | — | 3 | — | — | — | — | — | — | — | — | — | — |
| Cholesta-7-enol | — | — | — | — | — | — | — | — | — | — | — | — | — | — | — |
| Cholesteryl ester | — | — | — | — | — | — | — | — | — | — | — | — | — | — | — |
| 7-Dehydrocholesterol | — | — | — | — | — | — | — | — | — | — | — | — | — | — | — |
| Desmosterol (24-dehydrocholesterol) | — | 5 | — | 5 | 1 | 7 | 4 | 4 | — | 5 | 1 | 10 | 2 | 2 | 2 |
| 7-Dehydrodesmosterol | — | — | — | — | — | — | — | — | — | — | — | — | — | — | — |
| Zymosterol | — | — | 5 | 5 | 1 | 7 | 10 | 15 | — | 5 | 8 | 20 | 2 | 15 | 20 |
| 27-Hydroxycholesterol | — | — | — | — | — | — | — | — | — | — | — | — | — | 10 | — |
| Cholesta-7,24-dien-3-β-ol | — | — | — | — | — | — | — | — | — | — | — | — | — | — | — |
| Cholesta-8(9)-en-3-β-ol | — | — | — | — | — | — | — | — | — | — | — | — | 10 | — | — |

—Means none added to formulation.

TABLE 6

| Steroids | Formulations Numbers<br>Relative Ratios of Steroids in Formulations | | | | | | | | | | | | | | |
|---|---|---|---|---|---|---|---|---|---|---|---|---|---|---|---|
|  | 76 | 77 | 78 | 79 | 80 | 81 | 82 | 83 | 84 | 85 | 86 | 87 | 88 | 89 | 90 |
| Lanosterol | 10 | 10 | 10 | 10 | 10 | 10 | 10 | 10 | 5 | 5 | 5 | 5 | 5 | 5 | 5 |
| Dihydrolanosterol | 5 | 1 | 1 | 1 | 1 | — | — | — | — | — | — | — | — | — | — |
| 4,4-Dimethylcholesta-8(9),14,24-trien-3β-ol | 5 | 1 | 1 | 1 | 1 | 1 | 2 | 2 | 2 | 2 | 1 | 1 | 1 | 1 | — |
| 4,4-Dimethylcholesta-8,24-dien-3β-ol | 1 | 1 | 1 | — | — | 1 | 1 | 1 | — | — | 1 | 1 | 1 | 1 | — |
| 4,4-Dimethylcholesta-8(9),14-dien-3β-ol | — | — | — | — | — | — | — | — | 1 | — | — | — | 1 | 1 | 2 |
| 4,4-Dimethylcholesta-8-en-3β-ol | — | — | — | — | — | — | — | — | 1 | 2 | — | — | 1 | — | 1 |
| 14-Desmethyl lanosterol | — | — | — | — | — | — | — | — | — | — | — | — | — | — | — |
| Lathosterol | — | — | — | — | 1 | — | — | — | — | — | — | — | — | — | — |
| $\Delta^{7,24}$-Cholestadienol | — | 1 | 1 | 1 | — | 1 | 1 | — | 1 | 1 | 1 | 2 | 1 | — | 1 |
| Cholesterol | — | — | — | — | — | — | — | — | — | — | — | — | — | — | — |
| Cholesta-7-enol | — | — | — | — | — | — | — | — | — | — | — | — | — | — | — |
| Cholesteryl ester | — | — | — | — | — | — | — | — | — | — | — | — | — | — | — |
| 7-Dehydrocholesterol | — | — | — | — | — | — | — | — | — | — | — | — | — | — | — |
| Desmosterol (24-dehydrocholesterol) | — | — | — | 1 | 1 | 1 | 1 | 1 | — | — | 1 | 1 | — | 1 | — |

TABLE 6-continued

| Steroids | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|
| 7-Dehydrodesmosterol | — | — | — | — | — | — | — | — | — | — | — | — | — | — | — |
| Zymosterol | — | — | 1 | 1 | 1 | 1 | — | 1 | — | — | 1 | — | — | 1 | — |
| 27-Hydroxycholesterol | — | — | — | — | — | — | — | — | — | — | — | — | — | — | — |
| Cholesta-7,24-dien-3-β-ol | — | — | — | — | — | — | — | — | — | — | — | — | — | — | — |
| Cholesta-8(9)-en-3-β-ol | — | — | — | — | — | — | — | — | — | — | — | — | — | — | — |

—Means none added to formulation.

TABLE 7

Formulations — Relative Ratios of Steroids in Formulations

| Steroids | 91 | 92 | 93 | 94 | 95 | 96 | 97 | 98 | 99 | 100 | 101 | 102 | 103 | 104 | 105 |
|---|---|---|---|---|---|---|---|---|---|---|---|---|---|---|---|
| Lanosterol | 5 | 5 | 5 | 5 | 5 | 5 | 5 | 5 | 3 | 3 | 3 | 3 | 3 | 3 | 1 |
| Dihydrolanosterol | 1 | 1 | 1 | 1 | 1 | — | — | — | — | — | — | — | — | — | — |
| 4,4-Dimethylcholesta-8(9),14,24-trien-3β-ol | 1 | 1 | 1 | 1 | 1 | 1 | 2 | 2 | 2 | 2 | 1 | 1 | 1 | 1 | — |
| 4,4-Dimethylcholesta-8,24-dien-3β-ol | 1 | 1 | 1 | — | — | 1 | 1 | 1 | — | — | 1 | 1 | 1 | 1 | — |
| 4,4-Dimethylcholesta-8(9),14-dien-3β-ol | — | — | — | — | — | — | — | — | 1 | — | — | — | 1 | 1 | — |
| 4,4-Dimethylcholesta-8-en-3β-ol | — | — | — | — | — | — | — | — | 1 | 2 | — | — | 1 | — | — |
| 14-Desmethyl lanosterol | — | — | — | — | — | — | — | — | — | — | — | — | — | — | — |
| Lathosterol | — | — | — | — | 1 | — | — | — | — | — | — | — | — | — | — |
| $\Delta^{7,24}$-Cholestadienol | — | 1 | 1 | 1 | — | 1 | 1 | — | 1 | 1 | 1 | 2 | 1 | — | — |
| Cholesterol | — | — | — | — | — | — | — | — | — | — | — | — | — | — | — |
| Cholesta-7-enol | — | — | — | — | — | — | — | — | — | — | — | — | — | — | — |
| Cholesteryl ester | — | — | — | — | — | — | — | — | — | — | — | — | — | — | — |
| 7-Dehydrocholesterol | — | — | — | — | — | — | — | — | — | — | — | — | — | — | — |
| Desmosterol (24-dehydrocholesterol) | — | — | — | 1 | 1 | 1 | 1 | 1 | — | — | 1 | 1 | — | 1 | — |
| 7-Dehydrodesmosterol | — | — | — | — | — | — | — | — | — | — | — | — | — | — | — |
| Zymosterol | — | — | 1 | 1 | 1 | 1 | — | 1 | — | — | 1 | — | — | 1 | — |
| 27-Hydroxycholesterol | — | — | — | — | — | — | — | — | — | — | — | — | — | — | — |
| Cholesta-7,24-dien-3-β-ol | — | — | — | — | — | — | — | — | — | — | — | — | — | — | — |
| Cholesta-8(9)-en-3-β-ol | — | — | — | — | — | — | — | — | — | — | — | — | — | — | — |
| 5α-cholestan-3β-ol-6-one | 1 | 1 | 3 | 5 | — | — | — | — | — | — | — | — | 3 | 5 | 5 |
| 5α-cholestan-3β-ol-6-one | — | — | — | — | 5 | 5 | 5 | 5 | 1 | 5 | 5 | 3 | 5 | 5 | 5 |
| 5-cholesten-3β,25-diol | — | — | — | — | 5 | 5 | — | — | — | — | — | — | — | — | — |
| 5-cholesten-3β,25-OSO$_3$H (5-cholesten-3β,25-sulfate) | — | — | — | — | — | — | — | — | — | — | — | — | — | 1 | — |
| 5-cholesten-3β,25-diol, disulfate | — | 1 | 3 | 5 | — | — | — | 5 | 3 | 1 | 3 | — | — | — | 5 |
| 5-cholesten-3β-OSO$_3$H,25-ol (5-cholesten-3β-sulfate,25-ol) | — | — | — | — | — | — | — | — | — | 1 | 5 | — | — | — | — |

—Means none added to formulation.

TABLE 8

Formulations — Relative Ratios of Steroids in Formulations

| Steroids | 106 | 107 | 108 | 109 | 110 | 111 | 112 | 113 | 114 | 115 |
|---|---|---|---|---|---|---|---|---|---|---|
| Lanosterol | — | — | 1 | 1 | — | — | — | 1 | 1 | — |
| Dihydrolanosterol | — | — | — | — | — | — | — | — | — | — |
| Zymosterol | — | — | — | — | — | — | — | — | — | — |
| 5α-cholestan-3β-ol-6-one | 1 | 1 | 1 | 1 | 1 | — | — | — | — | — |
| 5α-cholestan-3β-ol-6-one | — | — | — | — | — | — | — | — | — | 1 |
| 5-cholesten-3β,25-diol | — | — | — | — | — | — | — | — | — | — |
| 5-cholesten-3β,25-OSO$_3$H (5-cholesten-3β,25-sulfate) | — | — | — | — | — | — | — | — | — | — |

TABLE 8-continued

| | Formulations Relative Ratios of Steroids in Formulations | | | | | | | | | |
|---|---|---|---|---|---|---|---|---|---|---|
| Steroids | 106 | 107 | 108 | 109 | 110 | 111 | 112 | 113 | 114 | 115 |
| 5-cholesten-3β,25-diol, disulfate | 1 | — | 1 | 1 | 1 | 1 | — | 1 | 1 | — |
| 5-cholesten-3β-OSO$_3$H,25-ol (5-cholesten-3β-sulfate,25-ol) | — | — | — | — | 1 | — | 1 | 1 | — | 1 |

—Means none added to formulation.

TABLE 9

| | Formulation Numbers Quantity of Steroids | | | | | |
|---|---|---|---|---|---|---|
| Steroids | 116 | 117 | 118 | 119 | 120 | 121 |
| Lanosterol | 50 mg | 30 mg | 50 mg | | | — |
| Sodium cholesteryl sulfate | — | 30 mg | 50 mg | 50 mg | — | 100 mg |
| 5-cholesten-3β,25-diol | 50 mg | 30 mg | | | 50 mg | 55 mg |

The use of the above representative formulations show that the disclosed methods are effective, or are improved, by at least 20%, at least 30%, at least 40%, at least 50%, at least 70%, at least 80% at least 90% or at least 95% over the results obtained in the absence of using the disclosed methods. In one aspect, the method reduces the severity of the cataract by at least 50%, at least 70%, at least 80% at least 90% or at least 95%.

EXPERIMENTALS

25-Hydroxycholesterol (5-cholesten-3β,25-diol, 5-cholestene-3β,25-diol), 98%, H1015 Sigma, CAS Number 2140-46-7; $C_{27}H_{46}O_2$, MW 402.65, Beilstein Registry Number 3161259. Sodium cholesteryl sulfate (5-cholesten-3β-ol sulfate sodium salt, cholesterol 3-sulfate sodium salt, cholesteryl sodium sulfate, cholesteryl sulfate sodium salt) C9523 Sigma, CAS Number 2864-50-8, $C_{27}H_{45}NaO_4S$, MW 488.70, Beilstein Registry Number 3899884. Lanosterol (3β-hydroxy-8,24-lanostadiene, 8,24-lanostadien-3β-ol) (≥93%, powder), L5768 Sigma, CAS Number 79-63-0, $C_{30}H_{50}O$, MW 426.72. DMSO (dimethyl sulfoxide, D1435), CAS Number 67-68-5. Acetonitrile, glycerine, carboxymethylcellulose, benzyl alcohol, phenyl-ethyl alcohol, potassium borate, potassium bicarbonate, Carbomer 980, polyhexamethylene biguanide (PHMB), phosphate buffer, Poloxamer 237, Polysorbate 80, castor oil, edetate disodium, sodium chloride, potassium chloride, polycaprolactone (PCL) polymer, lecithin, 1,2-distearoyl-sn-glycero-3-phosphoethanolamine-N-carboxy(polyethylene glycol) 2000 are commercially available, such as from Sigma-Aldrich.

Illustrative Formulations:

The formulations listed below are set forth for illustrative purposes only, and are not to be used to limit the proper construction of the claims. The formulations may comprise the steroids having different ratio in the compositions or formulations, such as those illustrated in Tables 1 to 9.

1. Aqueous Ophthalmic Composition for Treatment of Eye Disease: An illustrative formulation for treatment of eye disease, such as cataract, is set forth below:

Steroid Formulation No. 1:

Deionized water, 970 grams; glycerine (1.0%) 13 grams; a steroid formulation of Tables 1 to 8; carboxymethylcellulose (0.3%) 3 grams; benzyl alcohol (0.3%) 3 grams; potassium borate, 7.9 grams; potassium bicarbonate 3.4 grams or as needed to adjust the pH to 6.3-6.5.

2. Aqueous Ophthalmic Composition for Treatment of Eye Disease

Illustrative Steroid Formulation No. 2 employs benzyl alcohol and sodium buffers:

Steroid Formulation No. 2:

Deionized water 970 grams; glycerine (1.0%) 13 grams; a steroid formulation of Tables 1 to 8; carboxymethylcellulose (0.3%) 3 grams; phenyl-ethyl alcohol (0.3%) 3 grams; sodium borate 7.9 grams and sodium bicarbonate 3.4 grams or as needed to adjust the pH to 6.3-6.5.

3. Aqueous Ophthalmic Composition for Treatment of Eye Disease

Illustrative Steroid Formulation No. 3 employs Carbomer 980:

Steroid Formulation No. 3:

Deionized water, 970 grams; glycerine (1.0%) 13 grams; a steroid formulation of Tables 1 to 8; carbomer 980, 2 grams; benzyl alcohol (0.3%) 3 grams; potassium borate, 7.9 grams; potassium bicarbonate, 3.4 grams or as needed to adjust the pH to 6.3-6.5.

4. Aqueous Ophthalmic Composition for Treatment of Cataracts

An illustrative formulation for treatment of an eye disease, particularly cataract, is set forth below:

Steroid Formulation No. 4:

Deionized water, 970 grams; glycerine (1.0%) 13 grams; a steroid formulation of Tables 1 to 8; carboxymethylcellulose (0.3%) 3 grams; benzyl alcohol (0.3%) 3 grams; potassium borate 7.9 grams and potassium bicarbonate 3.4 grams or as needed to adjust the pH to 6.3-6.5.

Steroid Formulation No. 5:

Deionized water 970 grams; glycerine, 13 grams; a steroid formulation of Tables 1 to 8 (0.001 to 0.05 wt/vol %); p-aminobenzoic acid, 0.07 grams; carboxymethylcellulose, 3 grams; benzyl alcohol, 3 grams; potassium borate, 7.9 grams; potassium bicarbonate, 3.4 grams or as needed to adjust the pH to 6.3-6.5. Steroid Formulation No. 116:

116.A. Into a 30 ml glass beaker with a magnetic stir bar was added 50 mg of lanosterol, 50 mg of 5-cholesten-3β, 25-diol, 2.0 ml of absolute ethanol, 10 drops of DMSO and 8.0 ml of a stock sterile aqueous solution comprising 0.0001% polyhexamethylene biguanide (PHMB), phosphate buffer (0.2 wt/vol %), Poloxamer 237 (0.05 wt/vol %), edetate disodium (0.05 wt/vol %), sodium chloride (0.9 wt/vol %) and potassium chloride (0.05 wt/vol %) in double distilled water. The resulting solution was stirred at room temperature for 15 minutes where a small amount of insoluble beige particulates remain present as a suspension in the solution. The solution was transferred to a 10 ml sealable plastic (PET, LDPE) liquid dropper bottle and capped to seal the solution. The resulting bottle was sonicated in a water bath at room temperature for 40 minutes to disperse and dissolve the suspension, resulting in a homogeneous, slightly turbid solution.

116.B. Into a 30 ml glass beaker with a magnetic stir bar was added 50 mg of lanosterol, 50 mg of 5-cholesten-3β,25-diol, 2.0 ml of absolute ethanol, 10 drops of DMSO and 8.0 ml of a stock sterile aqueous solution comprising 0.0001% polyhexamethylene biguanide (PHMB), phosphate buffer (0.2 wt/vol %), Poloxamer 237 (0.05 wt/vol %), polysorbate 80 (0.1 wt/vol %), castor oil (0.1 wt/vol %), edetate disodium (0.05 wt/vol %), sodium chloride (0.9 wt/vol %) and potassium chloride (0.05 wt/vol %) in double distilled water. The resulting solution was stirred at room temperature for 15 minutes where a small amount of insoluble beige particulates remain present as a suspension in the solution. The solution was transferred to a 10 ml sealable plastic (PET, LDPE) liquid dropper bottle and capped to seal the solution. The resulting bottle was sonicated in a water bath at room temperature for 40 minutes to disperse and dissolve the suspension, resulting in a homogeneous solution.

Steroid Formulation No. 117:

117.A. Into a 30 ml glass beaker with a magnetic stir bar was added 30 mg of lanosterol, 30 mg of 5-cholesten-3β,25-diol, 30 mg sodium cholesteryl sulfate, 2.0 ml of absolute ethanol, 10 drops of DMSO and 8.0 ml of a stock sterile aqueous solution comprising 0.0001% polyhexamethylene biguanide (PHMB), phosphate buffer (0.2 wt/vol %), Poloxamer 237 (0.05 wt/vol %), edetate disodium (0.05 wt/vol %), sodium chloride (0.9 wt/vol %) and potassium chloride (0.05 wt/vol %) in double distilled water. The resulting solution was stirred at room temperature for 15 minutes where a small amount of insoluble off-white particulates remain present as a suspension in the solution. The solution was transferred to a 10 ml sealable plastic (PET, LDPE) liquid dropper bottle and capped to seal the solution. The resulting bottle was sonicated in a water bath at room temperature for 40 minutes to disperse and dissolve the suspension, resulting in a homogeneous, slightly turbid solution.

117.B. Into a 30 ml glass beaker with a magnetic stir bar was added 30 mg of lanosterol, 30 mg of 5-cholesten-3β,25-diol, 30 mg sodium cholesteryl sulfate, 2.0 ml of absolute ethanol, 10 drops of DMSO and 8.0 ml of a stock sterile aqueous solution comprising 0.0001% polyhexamethylene biguanide (PHMB), phosphate buffer (0.2 wt/vol %), Poloxamer 237 (0.05 wt/vol %), polysorbate 80 (0.1 wt/vol %), castor oil (0.1 wt/vol %), edetate disodium (0.05 wt/vol %), sodium chloride (0.9 wt/vol %) and potassium chloride (0.05 wt/vol %) in double distilled water. The resulting solution was stirred at room temperature for 15 minutes where a small amount of insoluble off-white particulates remain present as a suspension in the solution. The solution was transferred to a 10 ml sealable plastic (PET, LDPE) liquid dropper bottle and capped to seal the solution. The resulting bottle was sonicated in a water bath at room temperature for 40 minutes to disperse and dissolve the suspension, resulting in a homogeneous solution.

Steroid Formulation No. 118:

118.A. Into a 30 ml glass beaker with a magnetic stir bar was added 50 mg of lanosterol, 50 mg of sodium cholesteryl sulfate, 2.0 ml of absolute ethanol, 10 drops of DMSO and 8.0 ml of a stock sterile aqueous solution comprising 0.0001% polyhexamethylene biguanide (PHMB), phosphate buffer (0.2 wt/vol %), Poloxamer 237 (0.05 wt/vol %), edetate disodium (0.05 wt/vol %), sodium chloride (0.9 wt/vol %) and potassium chloride (0.05 wt/vol %) in double distilled water. The resulting solution was stirred at room temperature for 15 minutes where a small amount of insoluble beige particulates remain present as a suspension in the solution. The solution was transferred to a 10 ml sealable plastic (PET, LDPE) liquid dropper bottle and capped to seal the solution. The resulting bottle was sonicated in a water bath at room temperature for 40 minutes to disperse and dissolve the suspension, resulting in a homogeneous, slightly turbid solution.

118.B. Into a 30 ml glass beaker with a magnetic stir bar was added 50 mg of lanosterol, 50 mg of sodium cholesteryl sulfate, 2.0 ml of absolute ethanol, 10 drops of DMSO and 8.0 ml of a stock sterile aqueous solution comprising 0.0001% polyhexamethylene biguanide (PHMB), phosphate buffer (0.2 wt/vol %), Poloxamer 237 (0.05 wt/vol %), polysorbate 80 (0.1 wt/vol %), castor oil (0.1 wt/vol %), edetate disodium (0.05 wt/vol %), sodium chloride (0.9 wt/vol %) and potassium chloride (0.05 wt/vol %) in double distilled water. The resulting solution was stirred at room temperature for 15 minutes where a small amount of insoluble beige particulates remain present as a suspension in the solution. The solution was transferred to a 10 ml sealable plastic (PET, LDPE) liquid dropper bottle and capped to seal the solution. The resulting bottle was sonicated in a water bath at room temperature for 40 minutes to disperse and dissolve the suspension, resulting in a homogeneous solution.

Steroid Formulation No. 119:

119.A. Into a 30 ml glass beaker with a magnetic stir bar was added 50 mg of 5-cholesten-3β,25-diol, 50 mg of sodium cholesteryl sulfate, 2.0 ml of absolute ethanol, 10 drops of DMSO and 8.0 ml of a stock sterile aqueous solution comprising 0.0001% polyhexamethylene biguanide (PHMB), phosphate buffer (0.2 wt/vol %), Poloxamer 237 (0.05 wt/vol %), edetate disodium (0.05 wt/vol %), sodium chloride (0.9 wt/vol %) and potassium chloride (0.05 wt/vol %) in double distilled water. The resulting solution was stirred at room temperature for 15 minutes where a small amount of insoluble beige particulates remain present as a suspension in the solution. The solution was transferred to a 10 ml sealable plastic (PET, LDPE) liquid dropper bottle and capped to seal the solution. The resulting bottle was sonicated in a water bath at room temperature for 40 minutes to disperse and dissolve the suspension, resulting in a homogeneous, slightly turbid solution.

119.B. Into a 30 ml glass beaker with a magnetic stir bar was added 50 mg of 5-cholesten-3β,25-diol, 50 mg of sodium cholesteryl sulfate, 2.0 ml of absolute ethanol, 10 drops of DMSO and 8.0 ml of a stock sterile aqueous solution comprising 0.0001% polyhexamethylene biguanide (PHMB), phosphate buffer (0.2 wt/vol %), Poloxamer 237 (0.05 wt/vol %), polysorbate 80 (0.1 wt/vol %), castor oil (0.1 wt/vol %), edetate disodium (0.05 wt/vol %), sodium chloride (0.9 wt/vol %) and potassium chloride (0.05 wt/vol %) in double distilled water. The resulting solution was stirred at room temperature for 15 minutes where a small amount of insoluble beige particulates remain present as a suspension in the solution. The solution was transferred to a 10 ml sealable plastic (PET, LDPE) liquid dropper bottle and capped to seal the solution. The resulting bottle was sonicated in a water bath at room temperature for 40 minutes to disperse and dissolve the suspension, resulting in a homogeneous solution.

Steroid Formulation No. 120:

120.A. Into a 30 ml glass beaker with a magnetic stir bar was added 55 mg of 5-cholesten-3β,25-diol, 2.0 ml of absolute ethanol, 10 drops of DMSO and 8.0 ml of a stock sterile aqueous solution comprising 0.0001% polyhexamethylene biguanide (PHMB), phosphate buffer (0.2 wt/vol %), Poloxamer 237 (0.05 wt/vol %), edetate disodium (0.05 wt/vol %), sodium chloride (0.9 wt/vol %) and potassium chloride (0.05 wt/vol %) in double distilled water. The resulting solution was stirred at room temperature for 15 minutes where a small amount of insoluble beige particulates remain present as a suspension in the solution. The solution was transferred to a 10 ml sealable plastic (PET, LDPE) liquid dropper bottle and capped to seal the solution. The resulting bottle was sonicated in a water bath at room temperature for 40 minutes to disperse and dissolve the suspension, resulting in a homogeneous, slightly turbid solution.

120.B. Into a 30 ml glass beaker with a magnetic stir bar was added 55 mg of 5-cholesten-3β,25-diol, 2.0 ml of absolute ethanol, 10 drops of DMSO and 8.0 ml of a stock sterile aqueous solution comprising 0.0001% polyhexamethylene biguanide (PHMB), phosphate buffer (0.2 wt/vol %), Poloxamer 237 (0.05 wt/vol %), polysorbate 80 (0.1 wt/vol %), castor oil (0.1 wt/vol %), edetate disodium (0.05 wt/vol %), sodium chloride (0.9 wt/vol %) and potassium chloride (0.05 wt/vol %) in double distilled water. The resulting solution was stirred at room temperature for 15 minutes where a small amount of insoluble beige particulates remain present as a suspension in the solution. The solution was transferred to a 10 ml sealable plastic (PET, LDPE) liquid dropper bottle and capped to seal the solution. The resulting bottle was sonicated in a water bath at room temperature for 40 minutes to disperse and dissolve the suspension, resulting in a homogeneous solution.

Steroid Formulation No. 121:

121.A. Into a 30 ml glass beaker with a magnetic stir bar was added 100 mg of sodium cholesteryl sulfate, 2.0 ml of absolute ethanol, 10 drops of DMSO and 8.0 ml of a stock sterile aqueous solution comprising 0.0001% polyhexamethylene biguanide (PHMB), phosphate buffer (0.2 wt/vol %), Poloxamer 237 (0.05 wt/vol %), edetate disodium (0.05 wt/vol %), sodium chloride (0.9 wt/vol %) and potassium chloride (0.05 wt/vol %) in double distilled water. The resulting solution was stirred at room temperature for 15 minutes where a small amount of insoluble beige particulates remain present as a suspension in the solution. The solution was transferred to a 10 ml sealable plastic (PET, LDPE) liquid dropper bottle and capped to seal the solution. The resulting bottle was sonicated in a water bath at room temperature for 40 minutes to disperse and dissolve the suspension, resulting in a homogeneous, slightly turbid solution.

121.B. Into a 30 ml glass beaker with a magnetic stir bar was added 100 mg of sodium cholesteryl sulfate, 2.0 ml of absolute ethanol, 10 drops of DMSO and 8.0 ml of a stock sterile aqueous solution comprising 0.0001% polyhexamethylene biguanide (PHMB), phosphate buffer (0.2 wt/vol %), Poloxamer 237 (0.05 wt/vol %), polysorbate 80 (0.1 wt/vol %), castor oil (0.1 wt/vol %), edetate disodium (0.05 wt/vol %), sodium chloride (0.9 wt/vol %) and potassium chloride (0.05 wt/vol %) in double distilled water. The resulting solution was stirred at room temperature for 15 minutes where a small amount of insoluble beige particulates remain present as a suspension in the solution. The solution was transferred to a 10 ml sealable plastic (PET, LDPE) liquid dropper bottle and capped to seal the solution. The resulting bottle was sonicated in a water bath at room temperature for 40 minutes to disperse and dissolve the suspension, resulting in a homogeneous solution.

Alternative Topical Vehicle Solutions:

Double distilled $H_2O$ was added to 1.1 g $(EDTA)_2Na$ combined with 0.055 g alkyldimethylbenzylammonium chloride until a final volume of 1.1 L (pH 5.66) was achieved.

Excipients:

Sterile water (Ophthalmic grade isotonic solution, pH 6.3 to 6.5) buffered with potassium phosphate dibasic and potassium phosphate monobasic; benzyl alcohol (preservative); glycerin (lubricant) 1.0% and Carboxymethylcellulose sodium (lubricant) 0.3%.

Preparation of Drug-Loaded Nanoparticles:

A combination of a steroid formulation disclosed in Tables 1 to 8 is loaded into a lipid polymer hybrid nanoparticle through an adapted nano-precipitation method. The desired concentration of the steroid formulation is mixed with polycaprolactone (PCL) polymer dissolved in acetonitrile. Lecithin and 1,2-distearoyl-sn-glycero-3-phosphoethanolamine-N-carboxy(polyethylene glycol) 2000 (DSPE-PEG-COOH) are dissolved in a 4% ethanol aqueous solution at 20% of the PCL polymer weight and is heated above 60° C. The steroids/PCL solution is added into the preheated lipid solution under gentle stirring followed by rigorous vortexing for 3 min. The mixture solution is stirred for 2 h to allow the nanoparticles to form and the acetonitrile to evaporate. The nanoparticle solution is washed three times using an Amicon Ultra-4 centrifugal filter (Millipore) with a molecular weight cut-off of 10 kDa to remove the remaining organic solvent and free molecules.

The resulting nanoparticles are then re-suspended in PBS buffer for subsequent use. The size, size distribution and surface zeta potential of the drug-loaded nanoparticles are characterized by dynamic light scattering. The loading yield of the steroid formulation is quantified by high-performance liquid chromatography.

Treatment of Cataractous Lenses in Dogs:

The following adult dog breeds are used for assessing the treatment effect: black Labrador, Queensland Heeler and Miniature Pinscher. All dogs are adult, non-diabetic and have normal ocular surfaces and ocular adnexa, with naturally occurring adult onset cataracts. There are near equal distributions of male and female dogs. All exons of the LSS gene are screened in these dogs and there is no mutations. To assess the effect of the steroid formulation treatment on cataracts in live animals, dogs are pre-medicated with intramuscular injections of acepromaxine and butorphanol. After 20 min, induction of anesthesia is performed by application of intravenous propofol.

Dogs are then immediately intubated and maintained on oxygen and 2% isoflurane at 2 ltr/min. The steroid formulation (100 μg)-loaded nanoparticles are initially injected into the vitreous cavity in the test eye using a 28-gauge needle, and then are given every 3 days for the duration of the experiment. Treatment eyes or sham eyes are randomized. The control eye is given an injection with empty nanoparticle carriers as a negative control. The treatment eyes are treated with the steroid formulation in topical eye drops (see below for eye drop formulation). One 50-ml drop of steroid formulation is administered three times daily to the test eye over 6 weeks.

Degree of cataract severity is examined by slit lamp and photographed at the beginning and the end of the 6-week treatment period. Prior to examinations, pupils are dilated with 1% tropicamide and 10% phenylephrine. Degree of cataract severity is assessed by a blinded examiner and scored based on canine cataract stage. Improvements in lens clarity and transparency are quantified. Wilcoxon test is used to evaluate the treatment effect. Topical Vehicle Solution:

Double distilled water is added to 1.1 g (EDTA)$_2$Na combined with 0.055 g alkyldimethyl benzylammonium chloride until a final volume of 1.1 liters (pH 5.66) is achieved. 25 mM of the steroid formulation in the topical vehicle solution. Double distilled H$_2$O is added to a mixture of 12.5 g steroid formulation, 1.1 g (EDTA)$_2$Na, 0.055 g alkyldimethyl benzylammonium chloride and 200 ml EtOH to a final volume of 1.1 ltr. The vehicle solution was employed along with the additives and excipients as noted in the specific formulations.

Drug Formulations:

Dry formulations were prepared and provided in different labeled droppers. The formulations were prepared 3-5 days before administering the formulations to the dogs. The solutions were mixed only once and used for all experiments. When not used, the formulations were stored at room temperature and protected from light.

Canine Subjects:

Three dogs were administered with the selected formulations. The following adult dog breeds are used for assessing the treatment effect: Dog 1: Mixed breed; Dog 2: German Shepherd; Dog 3: Pekingese. Dogs are kept in indoor facilities, are very well fed and are treated completely humanely as adored house pets during the period of the experiments. None of the procedures employed in these experiments involve the exposure of the dogs to painful, stressful or noxious stimuli or processes.

Dog 1:

The treatment eyes, the left eyes (LE) and right eyes (RE), were treated with the two different formulations as follows: LE: Formulation 116.A; RE: Formulation 117.A.

Dog 2:

The treatment eyes, the left eyes (LE) and right eyes (RE), were treated with the two different formulations as follows: LE: Formulation 118.A; RE: Formulation 119.A.

Dog 3:

The treatment eyes, the left eyes (LE) and right eyes (RE), were treated with the two different formulations as follows: LE: Formulation 120.A; RE: Formulation 121.A.

Close-up photographs are taken of the eyes before any treatment. Photographs are also taken at the indicated time intervals on a daily and/or weekly basis, after 1 week, 2 weeks and 3 weeks. All photographs are recorded to identify the specific dog, the eyes (left eye (LE) or right eye (RE) and the formulations used. 1 Drop of the formulation (about 50 µl) is administered three times daily at about 7 AM, 1 PM and 4 PM, to the eyes, as indicated, over a period of 3 weeks.

Cataract grading system: Grade 0: absence of opacification (gridlines clearly visible); Grade 1: A slight degree of opacification (minimal clouding of gridlines, with gridlines visible); Grade 2: Presence of diffuse opacification involving almost the entire lens (moderate clouding of gridlines, with main gridlines visible); Grade 3: Presence of extensive, thick opacification involving the entire lens (total clouding of gridlines, with gridlines not seen at all).

Based on the results noted in the RESULTS table, the administration of the formulations provided at least 5% to 20% percent improvement in the clarity of the lens, restoring protein solubility, improving solubility of the α-crystallins, improving transparency and reversing protein aggregation.

Dog 1:

Lens clarity of LE at day 7 showed at least 20% improvement over untreated LE at day 1. Lens clarity of RE at day 7 showed at least about 15% improvement over untreated RE at day 1.

Formulations 116.A and 117.A may provide at least 10%, 20%, 30%, 40%, 50%, 60%, 70%, 80%, 100%, 110%, 120%, 130%, 150%, 170%, 200%, 220%, 240%, 260%, or 300% improvement in lens clarity over untreated lens. For example, dog lens with cataract grade 2 may improve to between grade 2 and grade 1, less than grade 1, or grade 0 after 1 week, 2 weeks, 3 weeks or 4 weeks with treatment with formulations 116.A and 117.A.

Dog 2:

Lens clarity of LE at day 7 showed at least 20% improvement over untreated LE day 1. Lens clarity of RE at day 7 showed at least about 15% improvement over untreated RE at day 1.

Formulations 118.A and 119.A may provide at least 10%, 20%, 30%, 40%, 50%, 60%, 70%, 80%, 100%, 110%, 120%, 130%, 150%, 170%, 200%, 220%, 240%, 260%, or 300% improvement in lens clarity over untreated lens. For example, dog lens with cataract grade 2 may improve to between grade 2 and grade 1, less than grade 1, or grade 0 after 1 week, 2 weeks, 3 weeks, or 4 weeks with treatment with formulations 118.A and 119.A.

Dog 3:

Lens clarity of LE at day 7 showed at least 5% to 20% improvement over untreated LE day 1. Lens clarity of RE at day 7 showed at least 5% to 20% improvement over untreated RE at day 1.

Formulations 120.A and 121.A may provide at least 10%, 20%, 30%, 40%, 50%, 60%, 70%, 80%, 100%, 110%, 120%, 130%, 150%, 170%, 200%, 220%, 240%, 260%, or 300% improvement in lens clarity over untreated lens. For example, dog lens with cataract grade 2 may improve to between grade 2 and grade 1, less than grade 1, or grade 0 after 1 week, 2 weeks, 3 weeks, or 4 weeks with treatment with formulations 120.A and 121.A.

As provided herein, the administration of the composition of the present application as disclosed herein is effective in reversing cataracts in a patient and the treatment significantly reduces cataract severity and increased lens clarity.

Pharmaceutical formulations can be prepared by procedures known in the art. For example, the compounds can be formulated with common excipients, diluents, or carriers, and formed into tablets, capsules, suspensions, powders, and the like. Examples of diluents that are suitable for systemic administration include water, saline and/or buffered physiological solutions. Also, physiological preservatives (e.g., benzalkonium chloride), antibiotics, and compounds to adjust the osmolarity of the formulation of the solution may be included.

Other fillers and carriers which may also be employed, depending upon the method of uptake, include the following: fillers and extenders such as starch, sugars, mannitol, and silicic derivates; binding agents such as carboxymethyl cellulose and other cellulose derivatives, alginates, gelatin and polyvinyl pyrrolidone; moisturizing agents such as glycerol; disintegrating agents such as agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

In one embodiment, the dose of steroids in a local concentration of the therapeutic steroids that may range from 0.005 µM to 50 µM, or from 0.05 nM to 1 µM, or from 1 nM to 100 nM; or as provided in the disclosed examples herein.

In one embodiment, in order to obtain sustained contact of the composition with the eye and increased delivery of the steroid formulation to the eye, the concentration in the lachrymal fluid and in the target tissue, may remain above the $MIC_{90}$ for the steroids. As used herein, the "effective residence time" means a period of time following application of the composition to the eye during which the concentration of the steroids in the lachrymal fluid and/or in the target tissue remains above the $MIC_{90}$ for the steroids. In one variation, no more than 3 drops, no more than 2 drops, or no more than 1 drop, each drop with of about 5 μl to about 50 μl, about 15 μl to about 30 μl, for example about 25 μl, may contain the desired dose of the steroids for administration to an eye. Administration of a larger volume to the eye may be possible, but risks loss of a significant portion of the applied composition by lachrymal drainage. In one variation, the composition is an in situ gellable aqueous composition or formulation, such as an in situ gellable aqueous solution. Such a composition comprises a gelling agent in a concentration effective to promote gelling upon contact with the eye or with lachrymal fluid in the exterior of the eye. In some circumstances, it may be advantageous to formulate a composition of the present application as a gel, to minimize loss of the composition immediately upon administration, as a result for example of lacrimation caused by reflex blinking.

In one variation, the formulation may further include at least one agent that improves ocular tolerance, such as aloe vera gel, a buffering agent and a tonicity modifier. In another variation, the formulation may include an antimicrobial agent and/or a preservative.

In certain embodiments, an appropriate amount of a calcium complexing agent such as ethylene diamine tetraacetic acid (EDTA) or a salt, such as a disodium salt of the agent, may be included in the composition to complex ions, such as calcium ions and prevent gel formation during storage. EDTA or a salt thereof may be included in an amount of about 0.01% to about 0.5%. Where a preservative is present, EDTA or a salt thereof may be included. In one aspect, disodium EDTA, in an amount of about 0.025% to about 0.1%, by weight, may be used to enhance antimicrobial activity.

A composition of the present application may contain an antimicrobially effective amount of a preservative, provided that the preservative does not substantially inhibit the effectiveness of the steroids or formulation or of any solubilizing agent in the composition. In one variation, the formulation may contain a preservative selected from the group consisting of imidazolidinyl urea in an amount of about 0.03% to about 0.5%; methylparaben in an amount of about 0.015% to about 0.25%; propylparaben in an amount of about 0.005% to about 0.01%; phenoxyethanol in an amount of about 0.25% to about 1%; disodium EDTA in an amount of about 0.05% to about 0.2%; thimerosal in an amount of 0.001% to about 0.15%; chlorobutanol in an amount of about 0.1% to about 0.5%; sorbic acid in an amount of about 0.05% to about 0.2%; benzalkonium chloride in an amount of about 0.001% to about 0.02%; any suitable combination of any of the above. All amount figures above are provided as a percent by weight of the total composition.

In another variation, the composition of the application may further comprise an ophthalmically compatible antioxidant. Such antioxidants may include sodium bisulfite, sodium metabisulfite, sodium thiosulfate, acetyl cysteine, cysteine, thioglycerol, sodium sulfite, acetone sodium bisulfite, dithioerythritol, dithiothreitol, thiourea, propyl gallate, methionine and erythorbic acid.

In another variation, the composition may further comprise glycerin in an amount of about 0.1% to about 5%, more preferably about 1% to about 2.5%, for example about 1.5% to about 2%, by weight. Glycerin can also be useful to increase viscosity of the composition and for adjustment of osmolality.

In another variation, the composition or formulation is a topical ophthalmic composition formulated for application to the eye, wherein the composition comprises a therapeutically effective amount of a steroid formulation as disclosed herein and a flowable crosslinked carboxy-containing polycarbophil mucoadhesive polymer, wherein the composition has a viscosity in the range of about 1,000 to about 3,400 cps and a pH of about 7.4 to about 8.5. In another variation of the composition, the flowable mucoadhesive polymer is in an amount of about 0.5% to about 1.5% by weight of the composition. In another variation, the steroid formulation is in an amount of about 0.005% to about 0.5% by weight of the composition.

The crosslinked or lightly crosslinked polymers of acrylic acid used in the present application are known in the art. In one embodiment, the polymers are prepared from at least about 90% or from about 95% to about 99.9% by weight, based on the total weight of monomers present, of one or more carboxyl-containing monoethylenically unsaturated monomers. Acrylic acid is a carboxyl-containing monoethylenically unsaturated monomer, but other unsaturated, polymerizable carboxyl-containing monomers, such as methacrylic acid, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), umbellic acid (p-hydroxycoumaric acid), and the like can be used in addition to or instead of acrylic acid. Such polymers are crosslinked by using less than about 5%, such as from about 0.5% or from about 0.1% to about 5%, or from about 0.2% to about 1%, based on the total weight of monomers present, of a polyfunctional crosslinking agent. Such crosslinking agents are non-polyalkenyl polyether difunctional crosslinking monomers such as divinyl glycol; 2,3-dihydroxyhexa-1,5-diene; 2,5-dimethyl-1,5-hexadiene; divinylbenzene; N,N-diallylacrylamide; N,N-diallylmethacrylamide and the like. Also included are polyalkenyl polyether crosslinking agents containing two or more alkenyl ether groupings per molecule, or alkenyl ether groupings containing terminal $H_2C=C<$groups, prepared by etherification of a polyhydric alcohol containing at least four carbon atoms and at least three hydroxyl groups with an alkenyl halide such as allyl bromide, such as polyallyl sucrose, polyallyl pentaerythritol; see for example U.S. Pat. No. 2,798,053. Diolefinic non-hydrophilic macromeric crosslinking agents having molecular weights of from about 400 to about 8,000, such as insoluble di- and polyacrylates and methacrylates of diols and polyols, diisocyanate-hydroxyalxyl acrylate or methacrylate reaction products, and reaction products of isocyanate terminated prepolymers derived from polyester diols, polyether diols or polysiloxane diols with hydroxyalkylmethacrylates, can also be used as the crosslinking agents; see U.S. Pat. Nos. 4,192,827 and 4,136,250.

The lightly crosslinked polymers may be made from a carboxyl-containing monomer or monomers as the sole monoethylenically unsaturated monomer present, together with a crosslinking agent or agents. The polymers can also be polymers in which up to about 40%, or from about 0% to about 20% by weight, of the carboxyl-containing monoethylenically unsaturated monomer or monomers has been replaced by one or more non-carboxyl-containing monoethylenically unsaturated monomers containing only physiologically and ophthalmologically innocuous substituents, including acrylic and methacrylic acid esters such as methyl methacrylate, ethyl acrylate, butyl acrylate, 2-ethylhexylacrylate, octyl methacrylate, 2-hydroxyethyl-methacrylate, 3-hydroxypropylacrylate, vinyl acetate, N-vinylpyrrolidone; see U.S. Pat. No. 4,548,990 for a listing of such additional monoethylenically unsaturated monomers. In one embodiment, polymers are lightly crosslinked acrylic acid polymers wherein the crosslinking monomer is 2,3-dihydroxyhexa-1,5-diene or 2,3-dimethylhexa-1,5-diene.

In one embodiment, the lightly crosslinked polymers used in the present specification may be prepared by suspension or emulsion polymerizing the monomers, using conventional free radical polymerization catalysts, to a dry particle size of not more than about 50 μm in equivalent spherical diameter; for example to provide dry polymer particles ranging in size from about 1 to about 30 μm, or from about 3 to about 20 μm, in equivalent spherical diameter. These polymers may range in molecular weight of about 25,000 to about 4,000,000, or about 500,000 to about 2,000,000.

In another variation, the formulation is an ophthalmic composition comprising a therapeutically effective amount of the steroid formulation and a flowable mucoadhesive polymer that is a crosslinked carboxy-containing polycarbophil, wherein the composition has a viscosity in the range of about 1,000 to about 3,400 cps and is formulated for administration to the eye of a mammal in drop form, the composition further comprises at least one additional non-steroidal anti-inflammatory agent, and the composition has a pH of about 7.4 to about 8.5.

In another variation, the formulation is an ophthalmic composition comprising a flowable mucoadhesive polymer and a therapeutically effective amount of the steroid formulation, wherein the composition has a viscosity formulated for administration to the eye of a mammal in drop form. In another variation, the steroid formulation is retained in or carried with the flowable mucoadhesive polymer. In another variation, the flowable mucoadhesive polymer is a sustained release delivery system. In another variation, the flowable mucoadhesive polymer is a carboxy-containing polymer, such as polycarbophil or DuraSite™. In another variation, the mucoadhesive polymer is in an amount of about 0.5% to about 1.5% by weight of the composition. In another variation, the polymer is in an amount of about 0.8% to about 1.0% by weight of the composition. In another variation, the steroid formulation is in an amount of about 0.005% to about 0.5% by weight of the composition. In another variation, the steroid formulation is in an amount of about 0.01% to about 0.2% by weight of the composition. In another variation, the steroid formulation is in an amount of about 0.045% to about 0.09% by weight of the composition. In another variation, the composition has a pH of about 7.4 to about 8.5, or a pH of about 8.3. In another variation, the viscosity of the composition is in the range of about 1,000 to about 2,000 centipoises (cps), or about 1,500 cps.

In another embodiment, there is provided a sustained release steroid delivery system, including a flowable mucoadhesive polymer and a therapeutically effective amount of the steroid formulation in an ophthalmic composition; wherein the flowable mucoadhesive polymer is in an amount of about 0.5% to about 1.5% by weight of the composition and the steroid formulation is in an amount of about 0.005% to about 0.5% by weight of the composition; or about 0.045% to about 0.09% by weight of the composition. In another variation, the steroid formulation is in an amount of about 0.01% to about 0.2% by weight of the composition. In another variation, the steroid formulation is retained in or carried with the flowable mucoadhesive polymer. In another variation, the flowable mucoadhesive polymer is a carboxy-containing polymer, such as polycarbophil or DuraSite™. In another variation, the steroid formulation is in an amount of about 0.01% to about 0.09% by weight of the composition, or about 0.8% to about 1.0% by weight of the composition. In another variation, the composition has a pH of about 7.4 to about 8.5, or about 8.3. In another variation, the viscosity of the composition is in the range of about 1,000 to about 2,000 cps, or about 1,500 cps.

In another embodiment, the disclosed formulations or compositions may contain one or more surfactants and, if desired, one or more adjuvants, including additional medicaments, buffers, antioxidants, tonicity adjusters, preservatives, thickeners or viscosity modifiers. The surfactants employed in the formulation may include POE sorbitan fatty acid esters, hydrogentated castor oils, Polysorbate 60, polyoxythylene hydrogenated castor oil, Polysorbate 80, Polyoxyethylene Hydrogenated Castor Oil 60 and Poloxamer 407, and mixtures thereof.

Additives in the formulation may include sodium chloride, EDTA (disodium edetate), and BAC (benzalkonium chloride) or sorbic acid, or both.

Compositions delivered by means of the sustained release medicament delivery system as disclosed herein may have residence times in the eye ranging from about 8 hours to about 24 hours. In one aspect, the steroid formulations contained in these compositions is released from the composition at rates that depend on such factors as the extent of steroid formulation loading and the pH of the system, as well as on any drug delivery adjuvants, such as ion exchange resins compatible with the ocular surface, where present. In another embodiment, the composition provides a sustained concentration of the steroid formulation of between $10^{-8}$ and $10^{-4}$ M, in another embodiment between $10^{-7}$ and $10^{-5}$ M, in the aqueous or treated tissue of the eye for at least one hour, at least two hours, and in certain embodiments, at least three hours or more. In another embodiment, the composition provides sustained concentration of the steroid formulation of between $10^{-8}$ and $10^{-4}$ M, or between $10^{-7}$ and $10^{-5}$ M, in the aqueous or treated tissue of the eye for at least two hours, at least three hours, or at least four hours or more.

In another embodiment, there is provided a process for the therapeutic treatment of the eye of a mammal including: (a) providing an ophthalmic composition comprising a steroid formulation in a therapeutically effective amount of about 0.005% to about 0.5% by weight of the composition and a flowable mucoadhesive polymer in an amount of about 0.5% to about 1.5% by weight of the composition; (b) administering the composition to the eye of a mammal in need thereof to treat a condition selected from cataracts, inflammation or inflammatory conditions of the eye.

In another embodiment, there is provided a composition or a method for combination therapy of the eye of a mammal comprising an ophthalmic composition having a therapeutically effective amount of a steroid formulation, a flowable mucoadhesive polymer such as DuraSite™ and one or more additional non-steroidal anti-inflammatory agent such as, a therapeutically effective amount of ketorolac. In one variation of the above, ketorolac is included in the composition of the invention in an amount of about 0.01% to about 1% by weight, about 0.4% to about 0.5% by weight of the composition. In one variation of the above, the formulation further comprises one or more agents selected from the group consisting of antibacterial agent, an antibacterial antibiotic agent, synthetic antibacterial agent, antifungal antibiotic agent, synthetic antifungal agent, antineoplastic agent, steroidal anti-inflammatory agent, non-steroidal anti-inflammatory agent, anti-allergic agent, glaucoma-treating agent, antiviral agent and anti-mycotic agent.

According to another embodiments, aspects and variations of the present application, the formulations or compositions may also include, in addition to the steroid as an active agent, one or more other active agents such as other NSAIDs. Suitable NSAIDs for combination therapy include aspirin, benoxaprofen, benzofenac, bucloxic acid, butibufen, carprofen, cicloprofen, cinmetacin, clidanac, clopirac, diclofenac, diflupredinate, etodolac, fenbufen, fenclofenac, fenclorac, fenoprofen, fentiazac, flunoxaprofen, furaprofen, flurbiprofen, furobufen, furofenac, ibuprofen, ibufenac, indomethacin, indoprofen, isoxepac, ketorolac, ketroprofen, lactorolac, lonazolac, metiazinic, miroprofen, nepafenac, naproxen, norketotifen, oxaprozin, oxepinac, phenacetin, pirprofen, pirazolac, protizinic acid, sulindac, suprofen, tiaprofenic acid, tolmetin, and zomepirac.

In another embodiment, the ophthalmic formulations may further comprise one or more additional therapeutically-active agents, including antibacterial antibiotics, synthetic antibacterials, antifungal antibiotics, synthetic antifungals, antineoplastic agents, steroidal anti-inflammatory agents, non-steroidal anti-inflammatory agents, anti-allergic agents, glaucoma-treating agents, antiviral agents, and anti-mycotic agents that may include their esters, alcohols and acids derived from the active agents.

Examples of the antibacterial antibiotics include aminoglycosides (e.g., amikacin, apramycin, arbekacin, bambermycins, butirosin, dibekacin, dihydrostreptomycin, fortimicin, gentamicin, isepamicin, kanamycin, micronomicin, neomycin, neomycin undecylenate, netilmicin, paromomycin, ribostamycin, sisomicin, spectinomycin, streptomycin, tobramycin and trospectomycin), amphenicois (e.g., azidamfenicol, chloramphenicol, florfenicol, thiamphenicol), ansamycins (e.g., rifamide, rifampin, rifamycin sv, rifapentine and rifaximin), β-lactams (e.g., carbacephems (e.g., loracarbef), carbapenems (e.g., biapenem, imipenem, meropenem and panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefinenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, ceifuzonam, cephacetrile sodium, cephalexin, cephaloglycin, cephaloridine, cephalosporin, cephalothin, cephapirin sodium, cephradine and pivcefalexin), cephamycins (e.g., cefbuperazone, cefmetazole, cefininox, cefotetan, cefoxitin), monobactams (e.g., aztreonam, carumonam, tigemonam), oxacephems, flomoxef and moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin and ticarcillin), other (e.g., ritipenem), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin and troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin and zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline and tetracycline), and others (e.g., cycloserine, mupirocin and tuberin).

Examples of the synthetic antibacterials include 2,4-diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol and nitrofurantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin and trovafloxacin), sulfonamides (e.g., acetyl sulfamethoxypyrazine, benzylsulfamide, chloramine-b, chloramine-t, dichloramine-t, 2-formylsulfisomidine, 4-β-d-glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfarnerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, 4-sulfanilamidosalicylic acid, 4-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine and sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium and thiazolsulfone), and others (e.g., clofoctol, hexedine, methenamine, methenamine anhydromethylene-citrate, methenamine hippurate, methenamine mandelate, methenamine sulfosalicylate, nitroxoline, taurolidine and xibornol).

Examples of the steroidal anti-inflammatory agents include 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

Examples of the antifungal antibiotics include polyenes (e.g., amphotericin b, candicidin, dennostatin, filipin, fungichromin, hachimycin, hamycin, lucensomycin, mepartricin, natamycin, nystatin, pecilocin and perimycin), others (e.g., azaserine, griseofulvin, oligomycins, neomycin undecylenate, pyrrolnitrin, siccanin, tubercidin and viridin). Examples of the synthetic antifungals include, but are not limited to: allylamines (e.g., butenafine, naftifine and terbinafine), imidazoles (e.g., bifonazole, butoconazole, chlordantoin, chlormiidazole, clotrimazole, econazole, enilconazole, fenticonazole, flutrimazole, isoconazole, ketoconazole, lanoconazole, miconazole, omoconazole, oxiconazole nitrate and sertaconazole, sulconazole and tioconazole), thiocarbamates (e.g., tolciclate, tolindate, tolnaftate), triazoles (e.g., fluconazole, itraconazole, saperconazole and terconazole) others (e.g., acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid and zinc propionate).

In another variation, the composition may further include at least one ophthalmically acceptable salt in an amount required to bring osmolality of the composition into an ophthalmically acceptable range. In some aspects, the salts can also be antioxidants. Salts suitable for use in adjusting osmolality include those having sodium, potassium or ammonium cations and chloride, citrate, ascorbate, borate, phosphate, bicarbonate, sulfate, thiosulfate or bisulfite anions; preferred salts include sodium chloride, potassium chloride, sodium thiosulfate, sodium bisulfite and ammonium sulfate. Other solutes suitable for adjustment of osmolality include sugars, for example dextrose, manitol, xylitol, and sucrose.

The composition of the present application may further include at least one ophthalmically acceptable pH adjusting agent and/or buffer, including an acid such as acetic, boric, citric, lactic, phosphoric and hydrochloric acids; a base such as sodium hydroxide, sodium phosphate, sodium borate, sodium citrate, sodium acetate, sodium lactate and tris-hydroxymethylaminomethane; and a buffer such as citrate/dextrose, sodium bicarbonate and ammonium chloride. Such an acid, base and/or buffer may be included in an amount required to maintain pH of the composition in an ophthalmically acceptable range.

The composition may further comprise a buffering agent and/or an agent for adjusting osmolality in amounts whereby the solution is substantially isotonic and has a physiologically acceptable pH. In another variation, the composition may further comprise at least one ophthalmically acceptable surfactant, such as a nonionic surfactant to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In another variation, the composition may further comprise an ophthalmically acceptable mucoadhesive polymer selected from the group consisting of hydroxypropylmethylcellulose, carboxymethylcellulose, carbomer (acrylic acid polymer), poly(methylmethacrylate), polyacrylamide, polycarbophil, polyethylene oxide, acrylic acid/butyl acrylate copolymer, sodium alginate and dextran. In another aspect of the composition, one or more antioxidants can be included to enhance chemical stability where required. Suitable antioxidants include ascorbic acid, sodium metabisulfite, sodium thiosulfate and thioglycerol.

In another embodiment, the disclosed composition may be administered as a solid, a paste, an ointment, a gel, a liquid, an aerosol, a mist, a polymer, a film, an emulsion, or a suspension. In another embodiment, the composition may be incorporated into or coated onto a contact lens or drug delivery device, from which one or more compounds from the composition is delivered by diffusion, away from the lens or device; or one or more compounds are released in a temporally-controlled manner. In the case that the contact lens is required for vision correction when the lens is in use, the contact lens comprising the composition may remain on the ocular surface or the eye. In another embodiment that employs a drug delivery device using the composition of the present application, the drug delivery device may be formed from biodegradable materials, or as permanent lens known in the art.

While a number of exemplary embodiments, aspects and variations have been provided herein, those of skill in the art will recognize certain modifications, permutations, additions and combinations and certain sub-combinations of the embodiments, aspects and variations. All references cited herein are incorporated by reference in their entirety. It is intended that the following claims are interpreted to include all such modifications, permutations, additions and combinations and certain sub-combinations of the embodiments, aspects and variations are within their scope.

What is claimed is:

1. An aqueous, isotonic ophthalmic composition comprising:
    a) a steroid selected from the group consisting of 5-cholesten-3β-OSO$_3$H,25-ol (5-cholesten-3β-sulfate,25-ol) and 5-cholesten-3β-ol sulfate sodium salt, or a pharmaceutically acceptable salt thereof; and
    b) a pharmaceutical excipient comprising 2-hydroxypropyl-β-cyclodextrin (CD) and hydroxypropyl methylcellulose (HPMC);
    wherein the amount of the steroid in the composition is in the range of 0.01% to 0.5% wt/wt.

2. The aqueous, isotonic ophthalmic composition of claim 1, wherein the pharmaceutically acceptable salt is a sodium salt.

3. The aqueous, isotonic ophthalmic composition of claim 1, wherein the compound is 5-cholesten-3β-OSO$_3$H,25-ol.

4. The aqueous, isotonic ophthalmic composition of claim 1, wherein the compound is 5-cholesten-3β-ol sulfate sodium salt.

5. A method for the treatment of cataracts, the method comprising an administration of an aqueous, isotonic ophthalmic composition comprising:
    a) a steroid selected from the group consisting of 5-cholesten-33-OSO$_3$H,25-ol (5-cholesten-3β-sulfate,25-ol) and 5-cholesten-3β-ol sulfate sodium salt, or a pharmaceutically acceptable salt thereof; and
    b) a pharmaceutical excipient comprising 2-hydroxypropyl-o-cyclodextrin (CD) and hydroxypropyl methylcellulose (HPMC);

wherein the amount of the steroid in the composition is in the range of 0.01% to 0.5% wt/wt;

to a patient in need thereof, wherein the administration of the composition reverses protein aggregation in cataracts or significantly reduces the severity of the cataract and increases the lens clarity, or inhibits aggresome formation of both wild-type and mutated crystalline proteins.

6. The method of claim 5, wherein the steroid is a sodium salt of 5-cholesten-3β-OSO$_3$H,25-ol.

7. The method of claim 5, wherein the steroid is 5-cholesten-3β-OSO$_3$H,25-ol.

8. The method of claim 5, wherein the steroid is 5-cholesten-3β-ol sulfate sodium salt.

* * * * *

UNITED STATES PATENT AND TRADEMARK OFFICE
CERTIFICATE OF CORRECTION

PATENT NO. : 10,398,709 B2
APPLICATION NO. : 15/221550
DATED : September 3, 2019
INVENTOR(S) : Sam L. Nguyen Page 1 of 1

It is certified that error appears in the above-identified patent and that said Letters Patent is hereby corrected as shown below:

In the Claims

Column 34 Claim 5, Line 62, "lesten-33-OSO3H,25-ol" should be replaced with -- lesten-3β-OSO3H,25-ol --.

Signed and Sealed this
Nineteenth Day of November, 2019

Andrei Iancu
*Director of the United States Patent and Trademark Office*